(12) United States Patent
Akhavan-Tafti et al.

(10) Patent No.: US 7,390,670 B2
(45) Date of Patent: *Jun. 24, 2008

(54) SIGNALLING COMPOUNDS AND METHODS FOR DETECTING HYDROGEN PEROXIDE

(75) Inventors: Hashem Akhavan-Tafti, Howell, MI (US); Robert A. Eickholt, Troy, MI (US); Kenneth S. Lauwers, Waterford, MI (US); Richard S. Handley, Canton, MI (US)

(73) Assignee: Lumigen, Inc., Southfield, MI (US)

( * ) Notice: Subject to any disclaimer, the term of this patent is extended or adjusted under 35 U.S.C. 154(b) by 301 days.

This patent is subject to a terminal disclaimer.

(21) Appl. No.: 10/371,053

(22) Filed: Feb. 20, 2003

(65) Prior Publication Data

US 2004/0166539 A1 Aug. 26, 2004

(51) Int. Cl.
G01N 21/76 (2006.01)
G01N 33/533 (2006.01)
C12Q 1/28 (2006.01)
C07F 5/02 (2006.01)
C07D 321/00 (2006.01)

(52) U.S. Cl. .......... 436/172; 436/546; 436/904; 435/28; 568/1; 549/213

(58) Field of Classification Search .......... 549/213; 436/904, 545, 546, 172; 435/28, 188; 568/1
See application file for complete search history.

(56) References Cited

U.S. PATENT DOCUMENTS

| 4,496,722 A * | 1/1985 | Gallop et al. .......... 544/69 |
| 4,659,817 A | 4/1987 | Gallop |
| 5,183,653 A | 2/1993 | Linder et al. |
| 5,242,842 A | 9/1993 | Sundrehagen |
| 5,506,144 A | 4/1996 | Sundrehagen |
| 5,512,451 A | 4/1996 | Kricka |
| 5,613,364 A | 3/1997 | Higgins |
| 5,629,168 A * | 5/1997 | Kricka .......... 435/28 |
| 5,723,295 A | 3/1998 | Akhavan-Tafti et al. |
| 5,739,318 A | 4/1998 | Frantzen |
| 5,922,558 A | 7/1999 | Akhavan-Tafti |
| 6,873,914 B2 * | 3/2005 | Winfield et al. .......... 702/19 |

FOREIGN PATENT DOCUMENTS

WO 02/46752 6/2002

* cited by examiner

Primary Examiner—Larry R. Helms
Assistant Examiner—Shafiqul Haq
(74) Attorney, Agent, or Firm—Richard S. Handley

(57) ABSTRACT

Methods and compound useful for detecting a source of hydrogen peroxide are disclosed wherein a signalling compound of the formula:

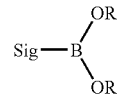

is reacted with peroxide. Sig is a non-polymeric organic group, B is a boron atom, and each R is independently selected from hydrogen, alkyl and aryl groups and can be joined together as a straight or branched alkylene chain forming a ring or as an aromatic ring. A detectable product compound of the formula Sig—OH or Sig—O⁻ is produced and detected by measuring color, absorbance, fluorescence, chemiluminescence, or bioluminescence. The signalling compound itself does not possess the detectable property or does so only to a very weak degree. The methods can be used as a detectable signal in assays for peroxide or peroxide-producing enzymes and in assays employing enzyme-labeled specific binding pairs.

33 Claims, 5 Drawing Sheets

SIGNALLING COMPOUNDS AND METHODS FOR DETECTING HYDROGEN PEROXIDE

FIELD OF THE INVENTION

The present invention relates to methods and compounds for detecting hydrogen peroxide. In particular, the present invention relates to signalling compounds which react with hydrogen peroxide to produce a detectable species. The invention further relates to assay methods for detecting hydrogen peroxide and for detecting peroxide-generating systems.

BACKGROUND OF THE INVENTION

1. Detection of Peroxide. Various methods are known for detecting hydrogen peroxide and related peroxides.

a. Colorimetric Detection of Peroxide. Compounds which react with hydrogen peroxide and a peroxidase to produce a colored product include ABTS, 4-aminoantipyrine (Anal. Letters, 26, 87 (1993)), and leuco dyes such as Leucocrystal Violet. Numerous methods exist for detecting hydrogen peroxide using a chromogen and a transition metal compound.

b. Fluorescent Detection of Peroxide. Compounds which react with hydrogen peroxide and a peroxidase to produce a fluorescent product include 2',7'-dichlorofluorescin, dihydrorhodamine 123 (Arch. Biochem. Biophys., 302(2), 348-55 (1993)) and N-acetylresorufin, (Chemical & Pharmaceutical Bulletin, 49(3), 294-29, (2001)).

c. Chemiluminescent Detection of Peroxide. Acridinium esters and sulfonamides undergo a rapid oxidation reaction with hydrogen peroxide at alkaline pH to produce a flash of chemiluminescence (e.g. U.S. Pat. Nos. 4,745,181, 4,946,958, 5,281,712 and 5,468,646). Lucigenin (9,9'-biacridinium dinitrate) is oxidized by hydrogen peroxide to produce chemiluminescence (Maskiewicz, et al., J. Am. Chem. Soc., 101, 5347-5354 (1979)).

Esters and amides of oxalic acid react with hydrogen peroxide in the presence of a fluorescer to produce chemiluminescence. This reaction formed the basis of the well-known "light stick" technology used in novelty items.

Cyclic acylhydrazides including the amine-substituted compounds luminol and isoluminol, hydroxy-substituted compounds and heterocyclic analogs react with hydrogen peroxide and a metal catalyst to produce chemiluminescence. Metal catalysts include heme, hexacyanoferrate and other transition metal ions including Cu(II) and Co(II).

U.S. Pat. No. 5,545,834 describes the chemiluminescent reaction of spiro-acridan compounds with hydrogen peroxide. The reaction is enhanced by the addition of horseradish peroxidase.

d. Enzymatic Detection of Peroxide. Various reagents have been developed for detection of peroxidase activity by reaction of a peroxidase enzyme, a source of hydrogen peroxide and an indicating reagent. These reagents therefore also serve to detect hydrogen peroxide. Color, fluorescence or chemiluminescence can be produced with use of the appropriate reagent. Chemiluminescent substrates include amino-substituted cyclic acylhydrazides such as the well-known luminol and isoluminol (Anal. Chim. Acta, 170, 101-107, (1985)), heterocyclic acylhydrazides (M. Ii, et al., Biochem. Biophys. Res. Comm., 193(2), 540-5 (1993); U.S. Pat. No. 5,324,835 and Y. Tominaga, et al., Tetrahedron Lett., 36, 8641-4 (1995)), and hydroxy-substituted phthalhydrazides (U.S. Pat. No. 5,552,298).

Applicant's U.S. Pat. Nos. 5,491,072, 5,523,212 and 5,593,845 disclose chemiluminescent N-alkylacridan-carboxylic acid derivatives which produce light upon reaction with a peroxide and a peroxidase. Applicant's U.S. Pat. No. 5,922,558 discloses a class of compounds containing an electron-rich double bond as chemiluminescent peroxidase substrates.

European Patent Specification EP0682254B1 discloses assay methods in which a conjugate of an enzyme that generates hydrogen peroxide is used and the peroxide is detected by acridinium ester chemiluminescence.

Fluorescent substrates for peroxidase include 3-(4-hydroxyphenyl)propionic acid as disclosed in U.S. Pat. No. 6,040,150,2-(4-hydroxyphenyl)acetic acid disclosed in Zaitsu and Ohkura, *Anal. Biochem.*, 109, 109-113 (1980), homovanillic acid and tyramine (Y. Li, et al., *Anal. Chim. Acta*, (340), 159-168, (1997)), o-phenylenediamine and N,N'-dicyanomethyl-o-phenylenediamine (Li, et al., *Microchem. J.*, 53(4), 428-436 (1996)), amide and carbamate derivatives of p-aminophenol (M. Kawaguchi, et al., *Bioluminescence and Chemiluminescence Perspectives for the 21st Century*, A. Roda et al., Eds., Wiley & Sons, Chichester, pp 508-511, (1999)), 3,4-dihydro-2(1H)-quinoxalone and related derivatives (Li, et al., *Anal. Chim. Acta*, 340(1-3), 159-168 (1997)), reduced forms of fluorescein, rhodamine and other xanthine dyes and fluorinated derivatives of the latter (U.S. Pat. No. 6,162,931).

Chromogenic or color-forming substrates for peroxidase include tetramethylbenzidine, chlorophenol red and 2,2'-Azino-bis-(3-ethylbenzthiazoline-6-sulfonic acid (Ngo, T. T. In *Immunochemistry of Solid-Phase Immunoassay*, Butler, J. E. Ed., CRC: Boca Raton, 1991, pp 85-102.).

2. Fluorescent and Colored Boronic Acid Sensors. Fluorescent and colored compounds containing boronic acid substituents for use in detection methods are disclosed in U.S. Pat. Nos. 4,496,722, and 4,659,817. The boronic acid group complexing compounds coordinate to and bind pairs of hydroxy, amine or thiol groups to form a fluorescent or colored complex. The binding partner can be either a carrier compound such as a buffer salt or it can be a biological substance which is to be tagged. Representative of the latter are cellular components. These methods differ fundamentally from the methods of the present invention by virtue of the unbound boronic acid compound being already colored or fluorescent to the same extent as the bound complex with the carrier or cellular component. Color or fluorescence is not created during the conduct of the methods.

The '772 and '817 patents also disclose peroxide assays in which the boronic acid substituted fluorescent or colored compounds are reacted with hydrogen peroxide to cleave the fluorescent or colored reporter moiety from the boronic acid group. Detection requires a separation step in order to measure the liberated reporter. Organic solvent extraction, release from a solid phase and filtration are disclosed as means to separate the released reporter from the reporter-boronic acid compound. Again, in contrast to the methods of the present invention, color or fluorescence is not created during the conduct of the methods.

Colored or fluorescent boronic acid complexing agents for use in detection of glycated blood proteins such as hemoglobin are disclosed in U.S. Pat. Nos. 5,242,842, 5,506,144 and 5,739,318. The boronic acid groups coordinate to and bind pairs of hydroxy groups to form a colored or fluorescent complex. The complex is separated from unbound complexing agent and measured. Detection does not involve any peroxide. This mode of measurement differs from the present invention in requiring a separation and that the unbound boronic acid compound is already colored or fluorescent to the same extent as the bound protein complex.

PCT Publication WO 02/46752 discloses assays for polyhydroxyl compounds, e.g. glucose, using boronic acid-quencher conjugates which bind to and quench the fluorescence of appropriately substituted fluorescers. Binding of the fluorescer via the boronic acid group of the quencher is reversed in the presence of the polyhydroxyl compound which competes for binding with the boronic acid group.

3. Phenylboronic acid Peroxidase Enhancers. U.S. Pat. Nos. 5,512,451 and 5,629,168 disclose phenylboronic acid compounds as enhancers of the peroxidase-catalyzed chemiluminescent oxidation of luminol with hydrogen peroxide. In the methods disclosed therein the boronic acid compound promotes the reaction of the peroxidase in oxidizing luminol. Chemiluminescence is produced from an oxidized form of luminol and not from the boronic acid. Arylboronic acid derivatives are disclosed as peroxidase enhancers in the chemiluminescent oxidations of acridan compounds in U.S. Pat. Nos. 5,723,295 and 5,922,558.

None of the foregoing methods disclose the use of boronic acid or boronate ester signalling compounds in a method for detecting and, when desired, quantifying the amount of hydrogen peroxide wherein the peroxide causes the formation of a detectable signal from the precursor signalling compound which does not itself possess the property being detected.

SUMMARY OF THE INVENTION

It is an object of the present invention to provide boronic acid or boronate ester signalling compounds which react with a source of hydrogen peroxide to produce a detectable product having a detectable property, which compounds do not possess the property being detected.

It is an object of the present invention to provide compounds which react with a source of hydrogen peroxide to produce a colored, fluorescent, chemiluminescent or bioluminescent product.

It is a further object of the present invention to provide methods for detecting a source of hydrogen peroxide employing the present compounds.

It is a further object of the present invention to provide methods for quantifying the amount of hydrogen peroxide by use of the above signalling compounds.

It is a further object of the present invention to provide methods for detecting enzymes which generate hydrogen peroxide by reaction of the enzyme with a substrate for the enzyme and detecting the hydrogen peroxide so generated by use of the above signalling compounds.

DESCRIPTION OF THE PREFERRED EMBODIMENTS

Figure 1:
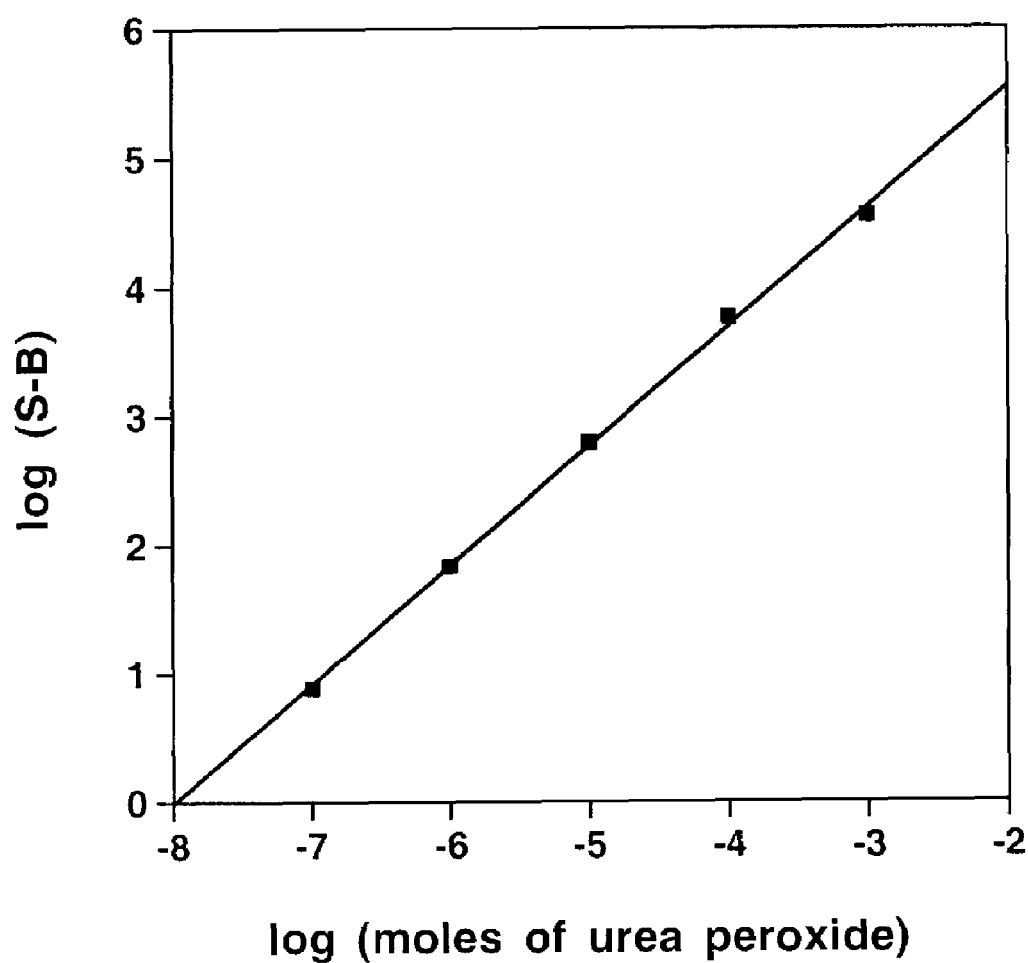
FIG. 1 is a graph relating the amount of hydrogen peroxide to the chemiluminescence intensity at 15 min emitted by 100 µL of a reagent described in Example 10. The term S-B refers to the chemiluminescence signal (S) in Relative Light Units (RLU) in the presence of hydrogen peroxide corrected for background chemiluminescence (B) in the absence of hydrogen peroxide.

Definitions:

Alkyl—A branched, straight chain or cyclic hydrocarbon group containing from 1-20 carbons which can be substituted with 1 or more substituents other than H. Lower alkyl as used herein refers to those alkyl groups containing up to 8 carbons.

Alkenyl—A branched, straight chain or cyclic hydrocarbon group containing at least one C—C double bond and containing from 2-20 carbons. Lower alkenyl as used herein refers to those alkenyl groups containing up to 8 carbons.

Alkynyl—A branched or straight chain hydrocarbon group containing at least one C—C triple bond and containing from 2-20 carbons. Lower alkynyl as used herein refers to those alkynyl groups containing up to 8 carbons.

Analyte—A substance the presence or amount of which is to be measured in a sample by an assay. Analytes include organic and biological molecules to which a specific binding partner having a specific binding affinity exists. Exemplary analytes include, without limitation, single stranded or double stranded DNA, RNA, DNA-RNA complexes, oligonucleotides, antibodies, antibody fragments, antibody-DNA chimeras, antigens, haptens, proteins, lectins, avidin, streptavidin and biotin. Other exemplary analytes also include hydrolytic enzymes, inhibitors of hydrolytic enzymes and dihydroxyaromatic compounds.

Aryl—An aromatic ring-containing group containing 1 to 5 carbocyclic aromatic rings, which can be substituted with 1 or more substituents other than H.

Biomedical analysis—Analyses of samples of biological origin for analytes of interest. The analyses can be immunoassays, western blots, northern blots, Southern blots, DNA hybridization assays, DNA sequence analysis, colony hybridizations, gene expression analysis, high throughput drug screening, detection of infectious agents or pathogens and the like.

Detectable signal—physical property resulting from measurement of the reaction product of the present reactions. The signal can be light produced by a chemiluminescent or bioluminescent reaction or by fluorescence. The signal can also be formation of color or a change of color or the change of absorption of ultraviolet or infrared radiation. The signal can also be a measurement of the molecular mass of the product or a specific signal in an NMR spectrum.

Halogen—Fluorine, chlorine, bromine or iodine atoms.

Heteroaryl or heteroaromatic—An aromatic ring-containing group containing 1 to 5 carbocyclic aromatic rings in which at least one of the ring carbon atoms is replaced with a nitrogen, oxygen or sulfur atom and which can be substituted with 1 or more non-H substituents.

Luminescent—capable of emitting light when excited to an electronic excited state. The light can be emitted either as fluorescence when decaying from a singlet excited state or as phosphorescence when decaying from a triplet excited state.

Peroxide—A compound containing an O—O bond, preferably hydrogen peroxide or a complex of hydrogen peroxide such as urea peroxide, perborate or percarbonate.

Sample—A fluid containing or suspected of containing one or more analytes to be assayed. Typical samples which are analyzed by the chemiluminescent reaction method are biological samples including body fluids such as blood, plasma, serum, urine, semen, saliva, cell lysates, tissue extracts and the like. Other types of samples include solvents, seawater, industrial water samples, food samples and environmental samples such as soil or water.

Source of hydrogen peroxide—a compound which is hydrogen peroxide or its salts such as sodium or potassium peroxide or hydrogen peroxide in complexed form such as urea peroxide, perborate salts and percarbonate salts.

Specific binding pair—Two substances which exhibit a mutual binding affinity. Examples include antigen-antibody, hapten-antibody or antibody-antibody pairs, complementary oligonucleotides or polynucleotides, avidin-biotin, streptavidin-biotin, hormone-receptor, lectin-carbohydrate, IgG-protein A, nucleic acid-nucleic acid binding protein and nucleic acid-anti-nucleic acid antibody.

Substituted—Refers to the replacement of at least one hydrogen atom on a group by a non-hydrogen group. It should be noted that in references to substituted groups it is intended that multiple points of substitution can be present unless clearly indicated otherwise.

Triflate—trifluoromethanesulfonate ester $CF_3SO_3$—.

The present invention concerns methods using signalling compounds which react with a source of hydrogen peroxide to produce a detectable compound capable of producing a detectable signal. The signalling compounds comprise one or more boronic acid or boronate ester groups situated on a signalling moiety designated Sig.

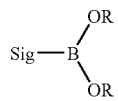

In the signalling compounds each R is independently selected from hydrogen, alkyl and aryl groups and can be joined together as a straight or branched alkylene chain forming a ring or as an aromatic ring. The group Sig is not readily detectable until the boron-containing group is replaced by a hydroxyl group through the reaction of hydrogen peroxide. Thus, reaction of the signalling compound with hydrogen peroxide replaces the boron-containing substituent with a hydroxyl group creating the detectable moiety. The product Sig-OH is readily distinguished from the starting signalling molecule by the creation of a detectable property. The starting signalling molecule itself does not possess the detectable property or does so only to a very weak degree so that the product is easily distinguished and quantifiable.

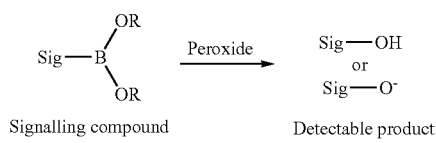

Signalling compound            Detectable product

Although the detectable product is depicted in the protonated form having a hydroxy group —OH, the detectable product can and in many cases will exist in the deprotonated form as the oxyanion or as an equilibrium mixture of protonated and deprotonated form. The exact form will be governed by factors such as reaction pH and electronic excitation which is known to ionize groups such as phenols by increasing their acidity in an electronic excited state. Both forms are considered to be within the scope of detectable product species in all embodiments of the invention.

Furthermore the present invention concerns methods of detecting hydrogen peroxide comprising reacting the signalling compounds with a source of hydrogen peroxide to produce a detectable product compound having a detectable property, detecting the product by measuring the detectable property and relating the detectable product to the hydrogen peroxide. The methods of the invention can be used in a quantitative fashion to determine the amount of hydrogen peroxide in a sample known or suspected to contain hydrogen peroxide. Such a method would comprise the steps of reacting the sample known or suspected to contain hydrogen peroxide with a signalling compound to produce a detectable product compound, detecting the detectable product compound by measuring a detectable property, and relating the detectable product to the amount of hydrogen peroxide.

Detectable properties which can be used to detect and thereby differentiate the product from the signalling compound reactant broadly comprise any physical property which is altered by the reaction with peroxide and include color or absorption of light of any suitable wavelength from ultraviolet to visible to infrared, fluorescence, chemiluminescence, bioluminescence, molecular mass, and other means directly influenced by molecular structure including nuclear magnetic resonance frequency (NMR), especially $^1H$ and $^{13}C$ NMR. Preferred properties permit quantification of the amount of hydrogen peroxide by quantifying the amount or fraction of the detectable product which is formed and are selected from color, absorbance, fluorescence, chemiluminescence, and bioluminescence. The detectable property of the product compound preferably differs from that of the signalling compound by at least a factor of ten, more preferably by at least a factor of 100 and still more preferably by at least a factor of 1000. Preferred detectable properties are selected from fluorescence, chemiluminescence and bioluminescence. Importantly, detection of the product can be performed in the presence of the reactant signalling compound and does not require a separation.

Sources of hydrogen peroxide include hydrogen peroxide and its salts such as sodium or potassium peroxide, and peroxide in complexed form such as urea peroxide, perborate salts, percarbonate salts and percarboxylic acids and their salts. Biological sources of hydrogen peroxide are included as hydrogen peroxide is known to be produced in vivo in leukocytes and certain antibodies. Sources of hydrogen peroxide also encompasses enzymatic generation systems as discussed below.

Signalling compounds useful in the methods of the invention comprise one or more boronic acid or boronate ester groups situated on a signalling moiety designated Sig. The group Sig can be any organic group capable of being detected as described above. Because of the near universality of detection of organic compounds by techniques such as NMR spectroscopy and mass spectrometry the nature of the Sig group encompasses essentially any non-polymeric organic group. Aliphatic, unsaturated, aromatic and heterocyclic groups can be used as the Sig group. The detectable property when using mass spectrometric detection is the molecular mass of the product which of course differs from that of the starting signalling compound by at least 27 mass units up to about 200 mass units depending on the nature of the groups $R^5$ and $R^6$.

The group Sig is limited only by the mass resolution of the measurement and the ability to detect the molecular ion. Sig groups having a molecular mass up to about 2000 will be detectable.

Detection by NMR spectroscopy allows detection of any reaction product Sig-OH which can be distinguished from the corresponding signalling compound. The detection can be performed by $^{13}C$ NMR analysis of the resonance frequency of the carbon undergoing the C—B to C—O bond change. Monitoring the change is most conveniently performed in $^{1}H$-decoupled mode so that the signal will be a singlet peak in most cases. The detection can also be performed by $^{1}H$ NMR analysis of the resonance frequency of a hydrogen atom on or near the carbon undergoing the C—B to C—O bond change. By near is meant that the hydrogen atom is substituted on another carbon atom or other atom within 1-3 atoms of the carbon undergoing the C—B to C—O bond change. Some examples of hydrogen atoms detectable by the present invention and useful in a qualitative or quantitative method for detecting the presence or amount of hydrogen peroxide are shown below.

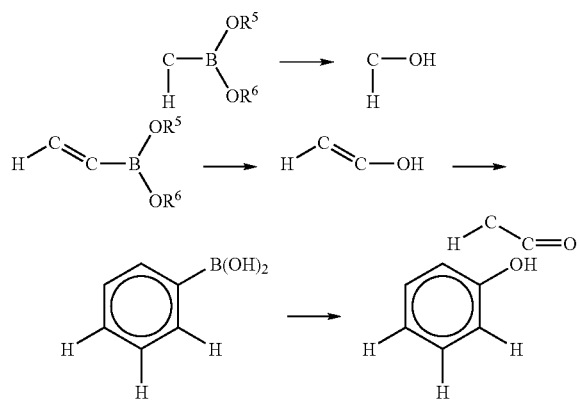

Signalling compounds detectable by NMR techniques when reacted in accordance with the present invention are preferably non-polymeric organic compounds wherein the Sig group has a molecular mass less than about 2000. Desirably the group Sig will not contain other atoms or groups which are chemically similar to the particular nucleus being detected and thereby obscure its detection. Quantification is readily achieved using NMR-based detection. A sample containing hydrogen peroxide is reacted with a signalling compound in an amount at least equal to the amount of the peroxide. The entire sample or a known fraction thereof is analyzed and the extent of conversion to the reaction product Sig-OH determined from the magnitude of the selected characteristic resonance signal.

A preferred class of groups for Sig comprises substituted and unsubstituted aromatic or heteroaromatic ring groups. Signaling compounds in this class generally possess a chromophore or fluorophore when converted to the product by reaction with a source of hydrogen peroxide and can therefore be used with an absorption or fluorescence detection scheme.

One group of signalling compounds comprise those boronic acid or boronate ester compounds which, upon conversion to the phenolic product Sig-OH through reaction with a source of hydrogen peroxide, become capable of generating chemiluminescence. Among the signalling compounds of the present invention which are converted to chemiluminescent products are a novel family of 1,2-dioxetane compounds. The previously unknown boronic acid or boronate ester substituted dioxetanes are of formula I:

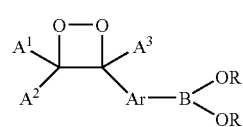

I wherein $A^1$-$A^3$ represent organic groups having from 1-20 carbon atoms and Ar is an aromatic or heteroaromatic ring group, wherein $A^1$ and $A^2$ or $A^1$ and $A^3$ or $A^3$ and Ar can be combined to form a ring, and each R is independently selected from hydrogen, alkyl and aryl groups and and can be joined together as a straight or branched alkylene chain forming a ring or as an aromatic ring. All such groups $A^1$-$A^3$, Ar and R can be substituted with non-hydrogen atoms. These compounds have been unexpectedly discovered to react with hydrogen peroxide to produce chemiluminescence.

A group of preferred 1,2-dioxetane compounds for detection of hydrogen peroxide by chemiluminescence have formula II:

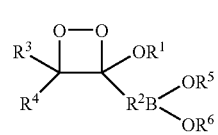

II wherein $R^1$ is is an organic group having from 1-20 carbon atoms which can be substituted with non-hydrogen atoms and can be combined with $R^2$ or $R^3$, $R^2$ is an aromatic or heteroaromatic ring group which can include additional substituents selected from halogens, alkyl, substituted alkyl, alkoxy, substituted alkoxy, carbonyl, carboxyl, amino and alkylamino groups, $R^3$ and $R^4$ are independently selected from acyclic and cyclic organic groups containing from 3-20 carbon atoms and which can be substituted with heteroatoms and $R^5$ and $R^6$ are independently selected from hydrogen, alkyl and aryl groups and and can be joined together as a straight or branched alkylene chain forming a ring or as an aromatic ring. In another group of compounds of formula II, $R^3$ and $R^4$ are combined together in a cyclic or polycyclic alkyl or alkenyl group which is spiro-fused to the dioxetane ring and contains 6 to 20 carbon atoms and which can include additional non-hydrogen substituents. A preferred polycyclic alkyl group is a substituted or unsubstituted adamantyl group.

A preferred group of compounds are boronic acids wherein $R^5$ and $R^6$ are both hydrogen atoms. Another preferred group of compounds contain an R group selected from substituted or unsubstituted phenyl and substituted or unsubstituted naphthyl groups. In another preferred group of compounds $R^1$ is a lower alkyl group which can be substituted with non-hydrogen atoms. In another preferred group of compounds $R^3$ and $R^4$ are each branched alkyl or cycloalkyl groups having from 3-20 carbon atoms. In another preferred group of compounds $R^3$ and $R^4$ are combined together as a spiro-fused polycyclic alkyl or alkenyl group and is more preferably an adamantyl group or a substituted adamantyl group having one or more substituent groups selected from halogens, alkyl, substituted alkyl, alkoxy, substituted alkoxy, carbonyl, carboxyl, phenyl, substituted phenyl, amino and alkylamino groups covalently bonded thereto.

Dioxetane compounds of formula I and II are converted by reaction with a source of hydrogen peroxide to the corresponding hydroxy-substituted dioxetane which produces chemiluminescence rapidly when in the deprotonated state.

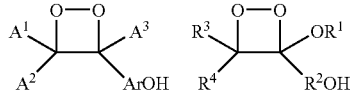

A large number of species are known to function in the method of the present invention and are encompassed within the class of compounds embodied by formula I. This knowledge is predicated in part on the knowledge that once a hydroxy-substituted dioxetane is formed by reaction of a boronic acid or boronate ester dioxetane derivative with peroxide, it will spontaneously decompose when deprotonated to produce light. Many such triggerable dioxetanes are known. Particular embodiments of compounds of formula I and II which react according to the present invention to produce chemiluminescence comprise those boronic acid or boronate ester dioxetanes which are converted by hydrogen peroxide to known hydroxy-substituted dioxetanes. These include, without limitation

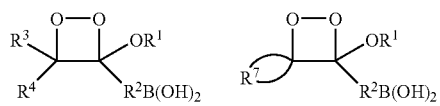

wherein $R^7$ is a cyclic or polycyclic alkyl or alkenyl group,

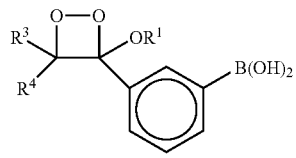

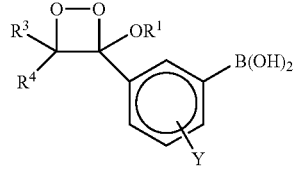

wherein Y is a substituent group selected from halogens, alkyl, substituted alkyl, alkoxy, substituted alkoxy, carbonyl, carboxyl, phenyl, substituted phenyl, amino and alkylamino groups,

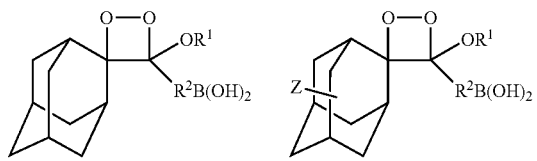

wherein Z is a substituent group selected from halogens, alkyl, substituted alkyl, alkoxy, substituted alkoxy, carbonyl, carboxyl, phenyl, substituted phenyl, amino and alkylamino groups,

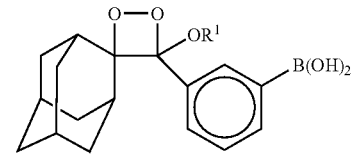

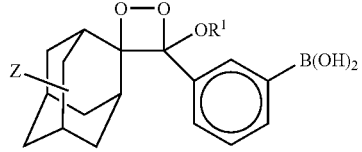

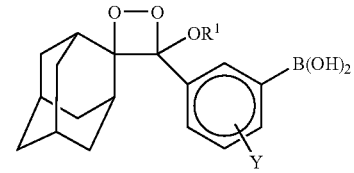

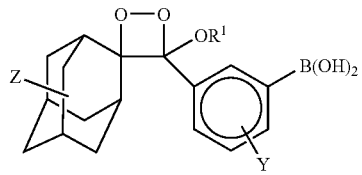

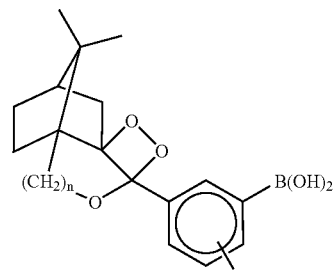

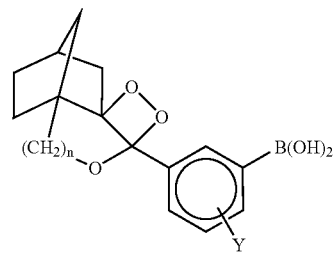

wherein n is from 1 to 3

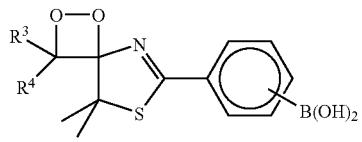

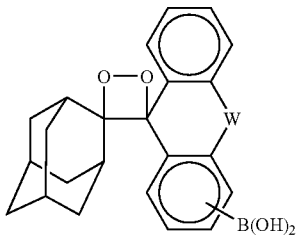

wherein W is O or S;

-continued
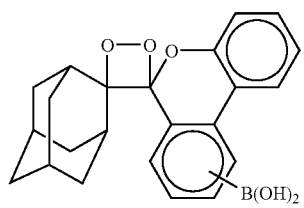
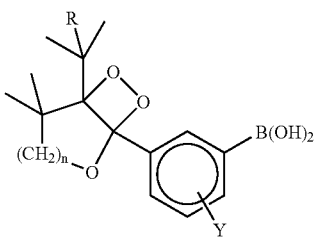
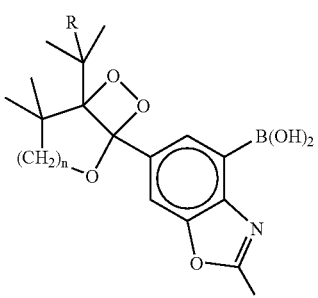
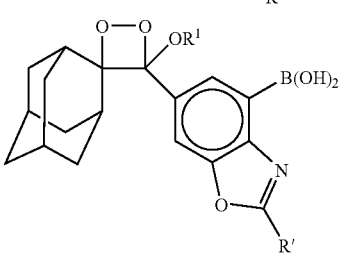
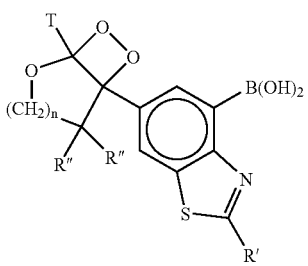
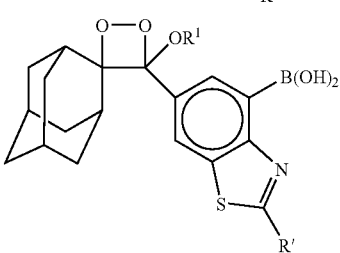
-continued
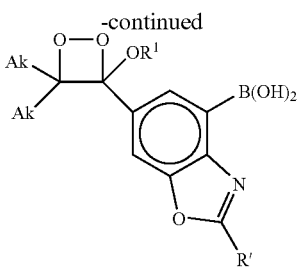
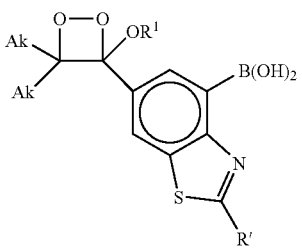
wherein n=1 or 2, R is selected from alkyl and benzyl and R' is selected from alkyl, phenyl and substituted phenyl; T is selected from alkyl, cycloalkyl and polycycloalkyl groups any of which can be substituted with non-hydrogen atoms, Ak is a branched alkyl or cycloalkyl group which can be substituted with non-hydrogen atoms,
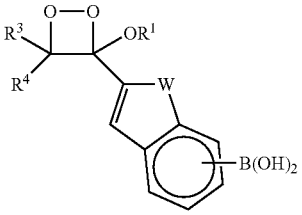
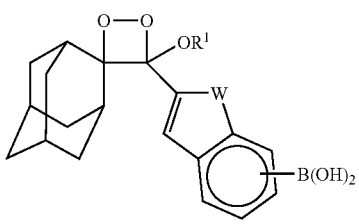
wherein W is O or S;
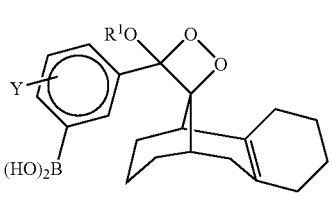

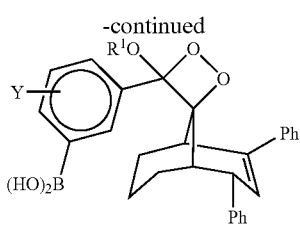

particularly where the group R¹ is lower alkyl or halogenated alkyl such as CH₃, CD₃, or CH₂CF₃ and Y is 4-choro or H

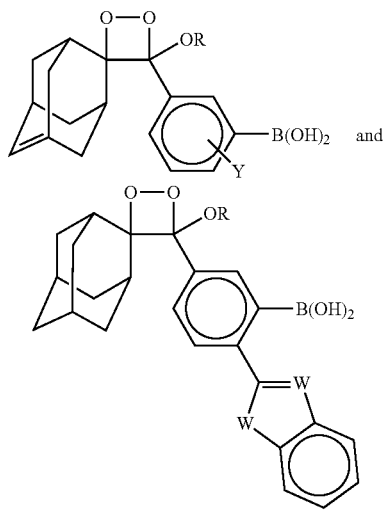

wherein W is O or S;

and boronate ester derivatives thereof as described above.

In addition to the foregoing structures, boronate ester analogs of these compounds are also useful in the practice of the present methods. In place of the B(OH)₂ group, the dioxetane compounds can contain a group having the formula B(OR)₂ wherein R can be an alkyl, specially a lower alkyl, e.g. methyl, ethyl, n-propyl, isopropyl, n-butyl, sec-butyl, t-butyl and the like or an aryl ring group such as phenyl. The R groups can be joined together in a ring e.g.

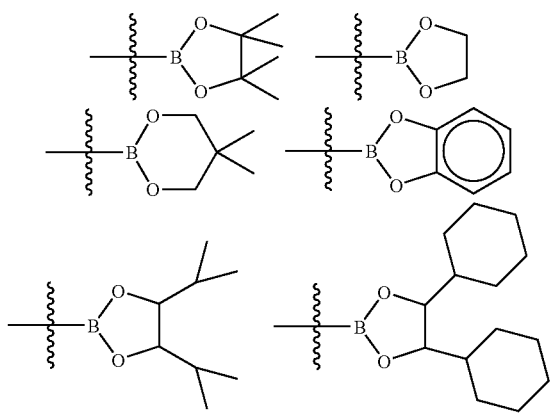

Another group of signalling compounds of formula I comprise dioxetane compounds substituted with a sulfur atom on the dioxetane ring. These include, without limitation

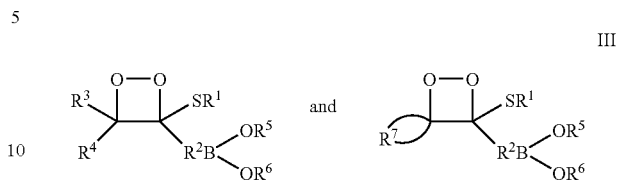

wherein R¹, R², R³, R⁴, R⁵, and R⁶ are as described above, and R⁷ is a cyclic or polycyclic alkyl or alkenyl group any of which can be substituted with non-hydrogen atoms. Particularly, signalling compounds of formula III comprise compounds in which R¹ is an organic group having from 1-20 carbon atoms which can be combined with R² or R³, R² is an aromatic or heteroaromatic ring group which can include additional substituents selected from halogens, alkyl, substituted alkyl, alkoxy, substituted alkoxy, carbonyl, carboxyl, amino and alkylamino groups, R³ and R⁴ are independently selected from acyclic and cyclic organic groups containing from 3-20 carbon atoms and which can be substituted with heteroatoms, and R⁵ and R⁶ are independently selected from hydrogen, alkyl and aryl groups and can be joined together as a straight or branched alkylene chain forming a ring or as an aromatic ring.

Preferred embodiments include without limitation

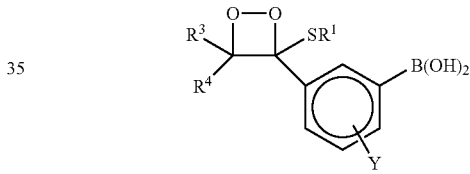

wherein Y is a substituent group selected from hydrogen, halogens, alkyl, substituted alkyl, alkoxy, substituted alkoxy, carbonyl, carboxyl, phenyl, substituted phenyl, amino and alkylamino groups,

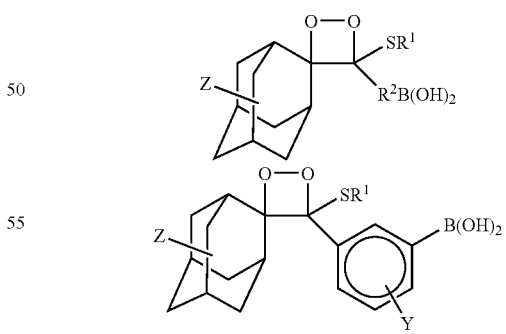

wherein Z is a substituent group selected from hydrogen, halogens, alkyl, substituted alkyl, alkoxy, substituted alkoxy, carbonyl, carboxyl, phenyl, substituted phenyl, amino and alkylamino groups.

Another aspect of the present invention is the use of a signalling compound including the compounds described above in a method to produce chemiluminescence by reaction with hydrogen peroxide. Reaction of the compound with hydrogen peroxide in an aqueous solution produces easily detected chemiluminescence when the reaction is conducted at alkaline pH. The reaction can be conducted optionally in the presence of a chemiluminescence enhancer.

In a preferred method of producing chemiluminescence, compound I or II is reacted with a peroxide in an alkaline solution with a pH of at least about 8 to produce chemiluminescence which commences upon reaction of the peroxide and compound I or II according to the reaction scheme.

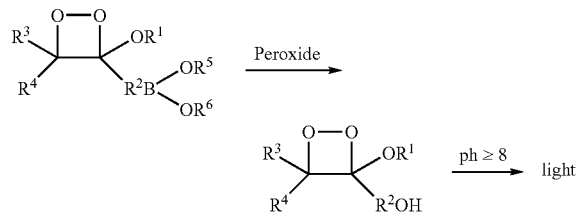

Reaction of the boronic acid or boronate ester-substituted dioxetane with hydrogen peroxide is believed to form a hydroxyaryl or aryloxide substituted dioxetane intermediate by replacing the carbon-boron bond with a carbon-oxygen bond. Under conditions in which of the phenolic OH group is at least partly ionized, decomposition of the dioxetane ensues with emission of light. The base or alkaline pH-triggered decomposition of hydroxyaryl substituted dioxetanes is well known in the art of chemiluminescence. Examples of such triggerable dioxetanes with various structural modifications are described in for example, U.S. Pat. Nos. 5,886,238, 6,036, 892, 6,284,899, 6,410,751, 5,650,525, 5,731,445, 5,877,333, 5,929,254, 6,218,135, 6,228,653, 5,013,827, 5,068,339, 5,652,345, 5,770,743, 5,132,204, 5,248,618, 5,603,868, 5,712,106, 6,107,036, 4,952,707, 5,089,630, 5,112,960, 5,220,005, 5,326,882, 5,330,900, 5,538,847, 5,543,295, 5,582,980, 5,591,591, 5,625,077, 5,679,802, 5,707,559, 5,773,628, 5,783,387, 5,831,102, 5,840,919, 5,843,681, 5,851,771, 5,869,699, 5,869,705, 5,871,938, 5,981,768, 6,022,964, 6,063,574, 6,132,956, 6,133,459, 6,140,495, 6,355,441 and 6,461,876. The boronic acid and boronate ester analogs of all of these dioxetanes are considered to fall within the scope of the present invention and are expressly included as part of the disclosure of the invention.

Chemiluminescence dan also be produced from the above signalling compounds by reaction with a source of hydrogen peroxide followed by reaction of the hydroxy-substituted dioxetane in an organic solvent with a strong base such as hydroxide ion or fluoride ion. Polar aprotic solvents such as DMSO, DMF and acetonitrile are preferred for producing highest intensity light.

Use of the above triggerable dioxetane signalling compounds of the present invention results in formation of a detectable product that can also be detected on the basis of the change in molecular mass and by $^1$H or $^{13}$C NMR as described above. Moreover it is recognized that the chemiluminescent reaction of the triggerable dioxetane signalling compounds results in a further fragmentation of the product in the process of producing chemiluminescence. It is recognized that the fragmentation or cleavage products can also be detected and/or quantified by molecular mass and by $^1$H or $^{13}$C NMR as described above. Other reaction products described below that are detectable by a chemiluminescent reaction also form subsequent products as the result of a fragmentation reaction or an oxidative dimerization process. These further products have unique molecular mass and NMR properties which can serve as the basis of detection.

Substances that are useful as chemiluminescence enhancers are those already known in the art of chemiluminescence. Included among these are quaternary onium salts alone or in combination with anionic surfactants such as alkyl sulfate salts and alkyl sulfonate salts. Quaternary onium salts include quaternary ammonium and phosphonium salts such as cetyltrimethylammonium bromide, dicationic surfactants as described in U.S. Pat. No. 5,451,437, polymeric phosphonium salts as described in U.S. Pat. No. 5,393,469, polymeric ammonium salts as described in U.S. Pat. No. 5,112,960, polymeric mixed phosphonium and ammonium salts and mixtures of polymeric ammonium salts and additives as described in U.S. Pat. No. 5,547,836.

A representative procedure for the synthesis of a boronic acid-substituted dioxetane useful as a chemiluminescent signalling compound is depicted below.

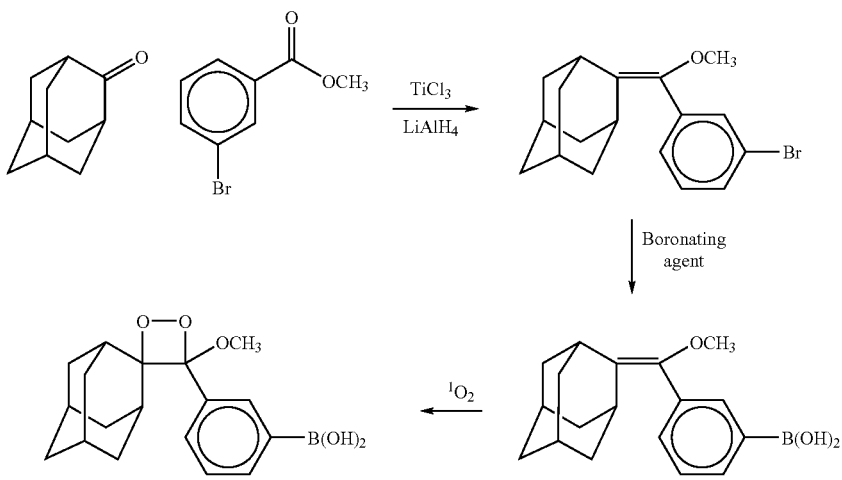

Additional chemiluminescent signalling compounds of the invention have the formulas below

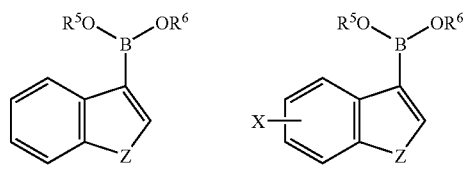 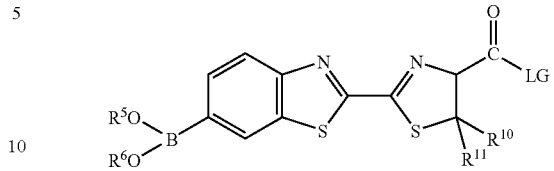

wherein Z is selected from O, S and $NR^8$, wherein $R^8$ is H or $Si(R^9)_3$, $R^9$ is $C_1$-$C_6$ alkyl or phenyl, and X represents one or two halogen substituents, preferably iodine, bromine or chlorine atoms. Reaction of the above signalling compounds with hydrogen peroxide replaces the boronic acid (or ester) substituent with a hydroxy group. Hydroxy-substituted indole compounds are described in e.g. U.S. Pat. No. 5,589,238 as undergoing a spontaneous chemiluminescent reaction with ambient oxygen.

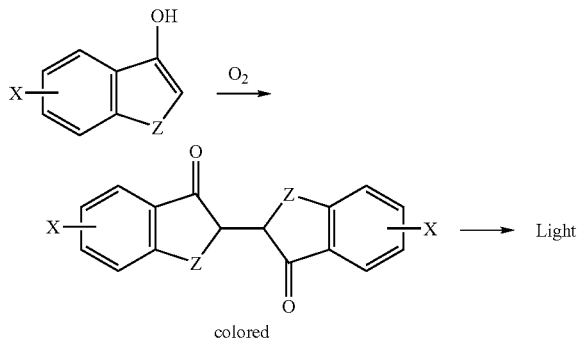

The above indolyl, benzofuranyl and benzothiophenyl boronic acid derivatives can also be used in embodiments where color is measured since the indigo-like dimerized products are highly colored. Moreover, the aforementioned U.S. Pat. No. 5,589,238 as well as European Patent Specification EP 0476930 B1 describe that this reaction also produces additional hydrogen peroxide, presumably through reduction of oxygen. Use of an indolyl, benzofuranyl or benzothiophenyl boronic acid signalling compound of the present invention will allow detection with greater sensitivity since the hydrogen peroxide will be recycled in the reaction. Stated another way, each molecule of hydrogen peroxide is capable of converting many molecules of signalling compound to detectable product.

Other chemiluminescent signalling compounds of the invention have the formula below

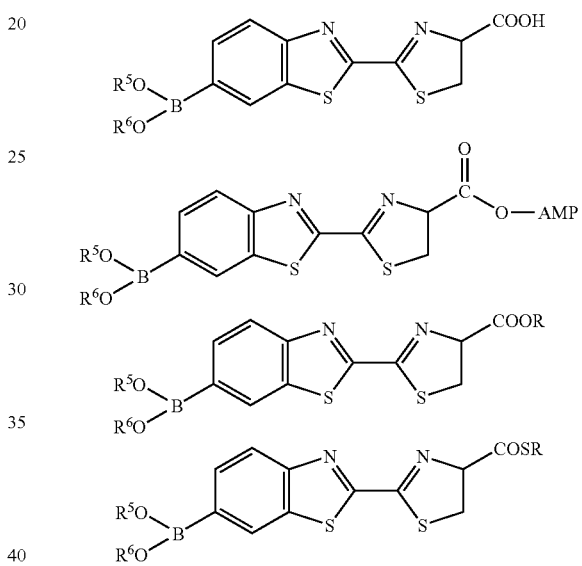

wherein LG is a leaving group and $R^{10}$ and $R^{11}$ are hydrogen, $C_1$-$C_4$ alkyl or are combined as an alkylene ring. Exemplary signalling compounds include the carboxylic acid, ester and thioester derivatives.

In the structure above, R is a substituted of unsubstituted alkyl or aryl group, and AMP designates adenosine monophosphate. Reaction of the boronic acid or ester moiety with hydrogen peroxide will produce the molecule known as firefly luciferin. This compound is known to react with the firefly luciferase enzyme to produce bioluminescence. It is also known to produce chemiluminescence upon treatment with strong base by an oxidative process involving molecular oxygen.

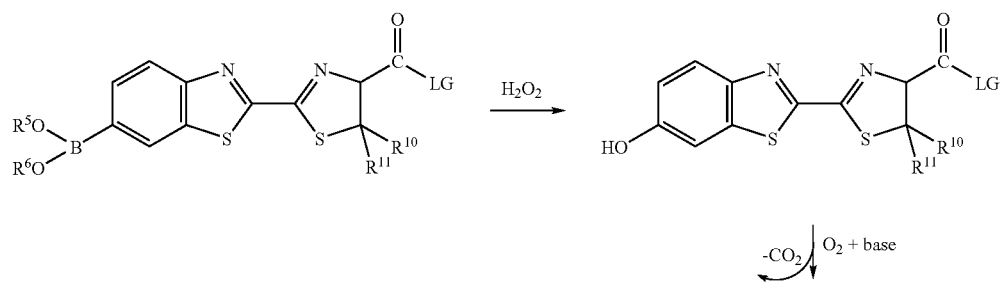

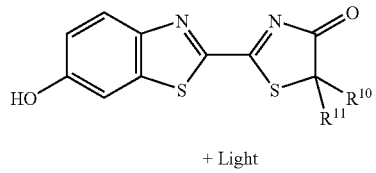

+ Light

Embodiments in which the leaving group is the AMP ester and the luciferase enzyme is used constitute a use of the present invention in a bioluminescent method to detect a source of hydrogen peroxide. Such a method comprises a) reacting a signalling compound with a source of hydrogen peroxide to produce a detectable product capable of undergoing a bioluminescent reaction;

b) reacting the detectable product with an enzyme and any necessary co-factors for the enzyme to produce bioluminescence; and c) detecting the bioluminescence.

The reaction can be conducted in different experimental modes. In one mode the carboxylic acid precursor can be reacted with peroxide in a first step to replace the boronic acid or ester with the hydroxyl group to produce the luciferin. The luciferin thus formed is then subjected to the art-known conditions for eliciting bioluminescence, reaction with firefly luciferase, $Mg^{+2}$ and ATP in a buffer. Since these two steps have differing pH optima, each step can be conducted at its optimum pH or they can be conducted at a single pH conducive to both reactions. In another mode of reaction the peroxide reaction is conducted concurrently with the luciferase/ATP reaction. reagents specifically identified for this purpose in U.S. Pat. Nos. 5,618,682, 5,650,289 and 5,814,471.

Another group of signalling compounds capable of being detected by chemiluminescence have the formula:

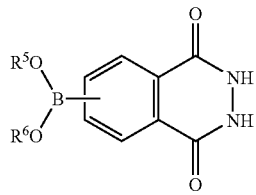

wherein $R^5$ and $R^6$ are as described above. Reaction of the compound above with a source of hydrogen peroxide converts the boronic acid or ester compound into the known hydroxyaryl hydrazide compound. The latter are known to undergo chemiluminescent reaction in aprotic solvent by reaction with strong base or in aqueous alkaline solution with additional peroxide and optionally with a transition metal catalyst or a peroxidase enzyme.

Another group of signalling compounds comprise those boronic acid or boronate ester signalling compounds which are converted to a fluorescent phenolic product Sig-OH through reaction with hydrogen peroxide. Among the signalling compounds of the present invention which are converted to fluorescent products are substituted and unsubstituted naphthaleneboronic acids and esters,

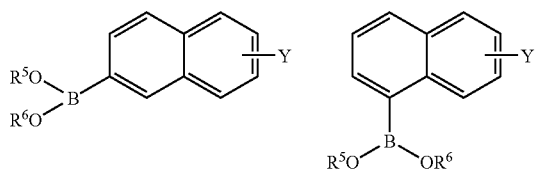

as well as the anthracene, phenanthrene and pyrene analogs, compounds of the formula which produce a coumarin or umbelliferone product,

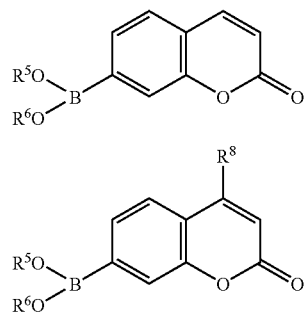

benzothiazole boronic acids and esters of the formula

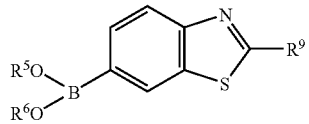

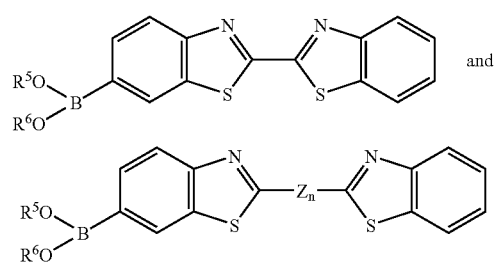

wherein Z is C—C double or triple bond or aromatic ring and n is 1 or 2, $R^9$ is a cyano, imine or carbonyl group, and compounds which generate other fluorescers including resorufin and fluorescein and having the structures below.

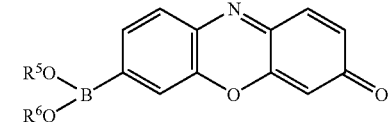

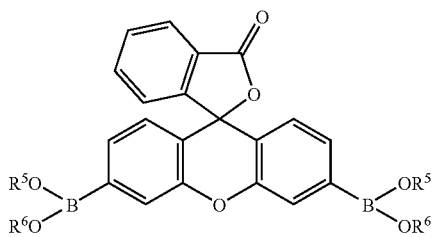

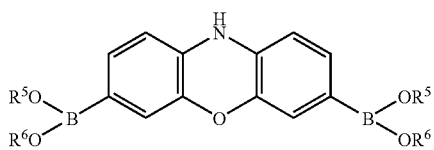

It should be recognized that the signalling compounds described above which produce a chemiluminescent product also can be detected by fluorescence. This situation arises because the emitter in a chemiluminescent reaction is, in nearly all cases, also fluorescent.

The above-mentioned signalling compounds which are converted to a fluorescent phenolic product Sig-OH are useful in a method for detecting a source of hydrogen peroxide comprising:

a) reacting a signalling compound with a source of hydrogen peroxide to produce a detectable product Sig-OH capable of detection by fluorescence;

b) irradiating the detectable product with light of a first wavelength; and c) detecting light emitted as fluorescence from the detectable product at a second wavelength different from the first wavelength.

Another group of signalling compounds comprise those boronic acid or boronate ester signalling compounds which are converted to a colored phenolic product Sig-OH through reaction with hydrogen peroxide. Among the signalling compounds of the present invention which are converted to colored products include, without limitation, the exemplary structures depicted below.

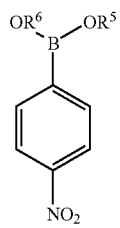 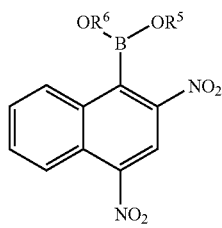

-continued

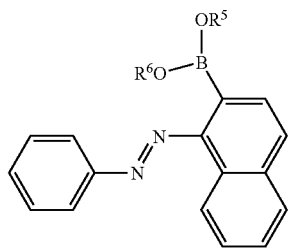

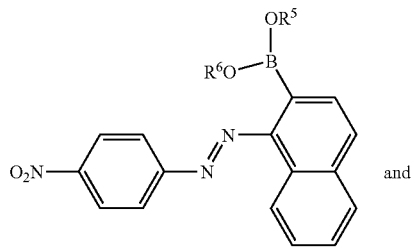
and

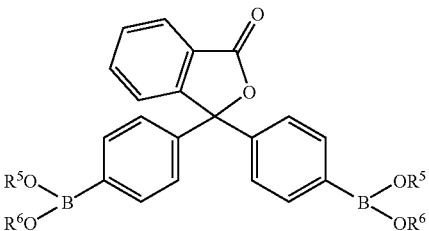

Numerous other colored compounds containing a phenol moiety are known in the art of colorimetric assays. Signalling compounds based on these structures but containing a boronic acid or boronate ester moiety in place of the hydroxyl group are explicitly considered to be within the scope of the invention.

The above-mentioned signalling compounds which are converted to a colored phenolic product Sig-OH are useful in a method for detecting a source of hydrogen peroxide comprising:

a) reacting a signalling compound with a source of hydrogen peroxide to produce a detectable product Sig-OH capable of detection by its color; and b) detecting the formation of the detectable product by the formation or change of color at a suitable wavelength or range of wavelengths.

Boronic acid and boronate ester compounds useful as signalling compounds as described herein are generally prepared by reaction of a boronating agent with an aryl halide or aryl triflate and a metal catalyst.

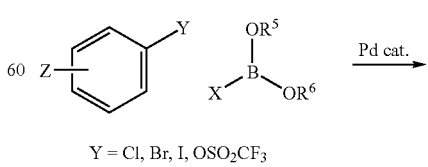

$Y = Cl, Br, I, OSO_2CF_3$
$X = H, OR, B(OR)_2$

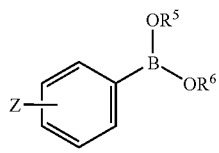

The metal catalyst is preferably a palladium compound used in the presence of a phosphorus compound capable of acting as a ligand on palladium. Representative palladium catalysts useful for effecting carbon-boron bond formation are well known in the art of synthetic organic chemistry and include divalent compounds $PdL_2$ with labile ligands L selected from carboxylate esters, halogens and ketones and include palladium acetate, palladium chloride, palladium bis(dibenzylideneacetone) $Pd(dba)_2$ and $Pd_2(dba)_3$.

Phosphine ligands include $PPh_3$, $PMe_3$, $PEt_3$, Pt—$Bu_3$, Pt—$Bu_2$Me, Pt—$Bu_2$Et, P(cyclohexyl)$_3$, BINAP and mixed alkylarylphosphines such as DPPE, DPPF, DPPB and DPPP. Bases include $KHPO_4$, $K_2CO_3$, $Na_2CO_3$, $CsCO_3$, CsF, $Et_3N$ and alkoxide salts such as sodium t-butoxide. Solvents useful in this step include toluene, benzene, THF, DME, diglyme and alcohol solvents including t-butanol and t-amyl alcohol.

Commonly used boronating agents include trialkyl borates such as trimethylborate, triethlborate and triisopropyl-borate, diboron compounds including bis(pinacolato)diboron, bis(neopentylglycolato)diboron.

The aromatic component is generally a bromide, iodide or triflate derivative of an aromatic hydrocarbon such as benzene, naphthalene, anthracene or pyrene or an aromatic heterocycle such as pyridine, quinoline, acridine, pyrrole, furan, benzofuran, thiophene, benzothiophene, oxazole, benzoxazole, thiazole, benzothiazole, xanthene, thioxanthene and phenothiazine any of which can be further substituted or unsubstituted.

Other methods of synthesizing boronic acids are known. Reaction of aryl bromide compounds with n-BuLi in THF at −78° C. produces an aryllithium compound which is reacted in situ with trimethyl borate or other trialkyl borates to produce the arylboronate ester. Hydrolysis to the arylboronic acid normally ensues during the reaction workup when trimethyl borate is employed.

Likewise Grignard reagents can be utilized in place of the aryllithium intermediates mentioned above in a method of synthesizing arylboronic acids and their esters. Reaction of the aryl Grignard reagent with a trialkyl borate in ether solvent produces the arylboronate ester.

Arylboronic acids and esters can also be prepared from an aromatic ring compound in a process using mercury-containing intermediates. Organomercury derivatives are converted to arylboronic acids (Q. Zheng, et al., Heterocycles, 37, 1761-72 (1994); N. Garg, et al., J. Am. Chem. Soc., 124, 13179 (2002)). For example, reaction of an indole compound with $Hg(OAc)_2$ produced the organomercurial Ar—Hg(OAc). Reaction of the latter with borane ($BH_3$-THF) followed by hydrolysis produced an indole-3-boronic acid.

Arylboronate esters can also be prepared from arenes according to the methods disclosed in Ishiyama, et al., J. Am. Chem. Soc., 124, 390-1 (2002). Reaction of an arene with an iridium catalyst with a bipyridyl or phenanthroline ligand and a dialkylborane or diboron compound effects direct borylation of the aromatic ring of the arene.

Reactions of signalling compounds of the present invention with peroxide are carried out in solution such as an organic solvent or an aqueous buffer or mixtures thereof. The reaction solution can be in contact with the surface of a solid support such as a bead, tube, membrane or microwell plate. Reactions involving the use of enzymes are conveniently performed in a buffer. Suitable buffers include any of the commonly used buffers capable of maintaining a pH in the range of about 6 to about 10 for example, phosphate, borate, carbonate, tris(hydroxymethylamino)methane ("tris"), glycine, tricine, 2-amino-2-methyl-1-propanol ("221"), diethanolamine and the like. The preferred method of practicing the invention in this regard is determined by the intended use.

The amount of time used for performing the reaction of the signalling compound with the source of hydrogen peroxide can vary over a wide range. Under conditions of alkaline solution reaction can be rapid, proceeding to completion in minutes. Under conditions of enzymatic generation of peroxide reaction times of hours can be used. Longer reaction times are not harmful even when the reaction is completed quickly. Conversely, short reaction times can be used even when it would not permit consumption of all of the peroxide.

Embodiments involving fluorescent or chemiluminescent products require the detection of light emission. Light emitted by the present method can be detected by any suitable known means such as a luminometer, x-ray film, high speed photographic film, a CCD camera, a scintillation counter, a chemical actinometer or visually. Each detection means has a different spectral sensitivity. The human eye is optimally sensitive to green light, CCD cameras display maximum sensitivity to red light, x-ray films with maximum response to either UV to blue light or green light are available. Choice of the detection device will be governed by the application and considerations of cost, convenience, and whether creation of a permanent record is required.

Signalling compounds of the present invention which produce light by means of fluorescence, chemiluminescence or bioluminescence typically emit light over a 100-200 nm wide band of emission, which exhibits a maximum intensity at wavelengths in the near ultraviolet to the visible region of the electromagnetic spectrum. Typical wavelengths of maximum intensity $\lambda_{max}$ in the range of 350-750 nm. It is contemplated that signalling compounds bearing a covalently linked fluorophore could undergo intramolecular energy transfer resulting in emission at longer wavelengths from the excited state of the fluorophore.

In a further embodiment, luminescent energy acceptors can be employed to shift the maximum emission to longer wavelengths (red-shifting) and/or to increase the quantity of luminescence emitted. Various techniques for red-shifting emission are known in the art of chemiluminescent reactions and assays. Covalently linked fluorophores are one example. Fluorescers can alternatively be added to the reaction solution as separate species. Fluorescers can be linked to a polymer or associated with a micelle or polymer in order to bring the fluorescer in close contact to the compound. Suitable energy transfer agents have an excited state at an energy level which overlaps that of the excited reaction product to permit the transfer of excitation energy and a fluorescent excited state which may or may not be the same as the excited state which overlaps that of the donor. Energy transfer agents useful for effecting singlet-singlet energy transfer are well known in the art of fluorescence. Energy transfer agents useful for effecting triplet-singlet energy transfer are also known in the art and usually possess at least one metal atom or other heavy atoms such as bromine or iodine atoms. Typical examples are 9,10-dibromoanthracene (DBA), sulfonated derivatives of DBA and $Ru(bpy)_3^{2+}$. Fluorescent energy transfer agents are evaluated empirically by comparing the intensity or wavelength of chemiluminescence produced in a reaction of a peroxide and a signalling compound as described above in the presence and absence of the agent.

Embodiments involving the formation of colored products require the detection of color or the absorption of light. Detection can be by any suitable known means. The simplest is visual observation of color development or color change. Photographic film or a digital camera can also be employed for this purpose. Embodiments requiring quantitative measurement of color will best be performed by spectrophotometry. Choice of the detection device will be governed by the application and considerations of cost, convenience, and whether creation of a permanent record is required.

The present invention includes the use of the methods and signalling compounds for detecting hydrogen peroxide in an assay procedure. Reaction of a signalling compound of the invention with a source of hydrogen peroxide produces the phenolic product which is detected by the appropriate means, i.e. color, absorbance, fluorescence or luminescence as described above. The magnitude of the signal is then related to the amount of peroxide present. Quantitative relationships are readily established by constructing calibration curves for any given signalling compound and a set of peroxide standards of known concentration. Uses for detection of hydrogen peroxide include the monitoring of biological or cellular processes, detection of antibodies which generate hydrogen peroxide, and the analysis of peroxide contamination in peroxide-forming solvents. Several of the signalling compounds of the present invention when dissolved in ether solvents such as p-dioxane rapidly give rise to detectable product, indicating the presence of peroxide contaminant.

In a further embodiment the present invention also relates to the use of these methods for detecting an enzyme which produces peroxide such as an oxidase enzyme or a dehydrogenase enzyme. It is well known that various enzymes in the class of oxidase enzymes produce hydrogen peroxide as a byproduct of the reaction which oxidizes its substrate. Known oxidase enzymes include galactose oxidase, glucose oxidase, cholesterol oxidase, amine oxidase, various amino acid oxidases, polyphenol oxidase, xanthine oxidase, uricase, alcohol dehydrogenase, lactate dehydrogenase, malate dehydrogenase, glyceraldehyde-3-phosphate dehydrogenase, glycerol dehydrogenase, and glucose-6-phosphate dehydrogenase. In practice, the oxidase enzyme is reacted with a substrate for the oxidase enzyme to produce hydrogen peroxide. Either concurrently or after a suitable time period, the accumulated hydrogen peroxide is reacted with a signalling compound of the invention to produce the phenolic product which is detected by the appropriate means as described above. Further the oxidase or dehydrogenase enzyme can be present as a conjugate to a biological molecule or a member of a specific binding pair in an assay for an analyte.

An important use of the present methods in biomedical and other analysis is for detecting the presence or amount of an analyte in an assay procedure by a chemiluminescent, fluorescent, bioluminescent or color-forming reaction. One format comprises using an oxidase or dehydrogenase enzyme as a label on a specific binding pair member. An example is an enzyme-linked immunoassay, such as the so-called enzyme-linked immunosorbent assay or ELISA. Such assays fall broadly into two categories. Competitive assays feature an immunological binding of a specific antibody with the analyte and an analyte analog, e.g. a detectably labeled analyte molecule. Sandwich assays result by the sequential or simultaneous binding of two antibodies, one of which is detectably labeled, with the analyte. The detectably labeled binding pair so formed is assayed with the compounds and methods of the present invention. When the detectable label is the oxidase enzyme, it is detected directly. When the detectable label is a member of another specific binding pair, e.g. a hapten, a conjugate of its binding partner with an oxidase is reacted first and the oxidase then detected in accordance with the present methods. Measurement can be performed with enzyme-labeled species in a solution or attached to a solid surface or support including beads, tubes, microwells, magnetic particles, test strips, membranes and filters such as are in common use in the art. Other exemplary uses are the detection of proteins by the technique of Western blotting and nucleic acids by the use of enzyme-labeled nucleic acid probes including Southern blotting, northern blot analysis of RNA, and DNA sequencing.

Detection of the oxidase-labeled specific binding pair formed in the assay is conducted by supplying a substrate for the oxidase enzyme and, either concurrently or subsequently, supplying a signalling compound of the invention. Reaction of the oxidase with its substrate produces hydrogen peroxide. The hydrogen peroxide reacts with the signalling compound to produce the phenolic product which is detected by the appropriate means as described above.

The method comprises the steps of contacting a sample suspected of containing the analyte with a signalling compound of the present invention and a source of hydrogen peroxide, and detecting the phenolic product by means of chemiluminescence, fluorescence, bioluminescence or color in a qualitative method. If quantitation is desired, the amount of phenolic product formed is related to the amount of the analyte. The relationship between the detectable signal and amount of analyte can be easily discerned by constructing a calibration curve with known amounts of the analyte. The signalling compound is typically used in a concentration of about $10^{-8}$ M to about $10^{-2}$ M, preferably between about $10^{-6}$ M and about $10^{-3}$ M. Typical samples which can be analyzed by the present methods are body fluids such as blood, plasma, serum, urine, semen, saliva, sputum, cerebrospinal fluid and the like.

The present invention also includes embodiments wherein the signalling compound contains a labelling group other than the boronic acid group which permits labeling on a substance to be detected. The labeling group comprises a group having the formula -L-RG wherein L is a linker and RG is a reactive group.

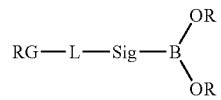

IV

The group L is a linking group which can be a bond or another divalent or polyvalent group, the group RG is a reactive group which enables the signalling compound to be linked to another compound.

The linking group can be a bond, an atom, or a straight, or branched chain of atoms some of which can be part of a ring structure. The substituent usually contains from 1 to about 50 non-hydrogen atoms, more usually from 1 to about 30 non-hydrogen atoms. Atoms comprising the chain are selected from C, O, N, S, P, Si, B, and Se atoms, preferably from C, O, N, P and S atoms. Halogen atoms can be present as substituents on the chain or ring. Typical functional groups comprising the linking substituent include alkylene, arylene, alkenylene, ether, peroxide, carbonyl as a ketone, ester, carbonate ester, thioester, or amide group, amine, amidine, carbamate, urea, imine, imide, imidate, carbodiimide, hydrazine, diazo, phosphodiester, phosphotriester, phosphonate ester, thioether, disulfide, sulfoxide, sulfone, sulfonate ester, sulfate ester, and thiourea groups.

The reactive group RG is an atom or group whose presence facilitates bonding to another molecule by covalent attachment or physical forces. In some embodiments, attachment of a signalling compound of the present invention to another compound will involve loss of one or more atoms from the reactive group, e.g. when the reactive group is a leaving group such as a halogen atom or a tosylate group and the signalling compound bonds to another compound by a nucleophilic displacement reaction. In other embodiments, attachment of a signalling compound to another compound by covalent bond formation will involve reorganization of bonds within the reactive group as occurs in an addition reaction such as a Michael addition or when the reactive group is an isocyanate or isothiocyanate group. In still other embodiments, attachment will not involve covalent bond formation, but rather physical forces in which case the reactive group remains unaltered. By physical forces is meant attractive forces such as hydrogen bonding, electrostatic or ionic attraction, hydrophobic attraction such as base stacking, and specific affinity interactions such as biotin-streptavidin, antigen-antibody and nucleotide-nucleotide interactions.

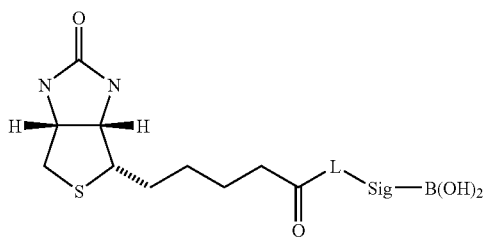

The structure above bearing a biotin moiety as a reactive group exemplifies a compound capable of specific binding interactions by non-covalent means. Numerous specific linking groups and reactive groups are listed in U.S. Pat. No. 6,126,870.

The present invention also includes embodiments wherein the signalling compound is provided as a label on a substance to be detected. By this is meant conjugates of a substance which is to be detected and at least one signalling compound IV bearing a labeling substituent.

In order to more fully describe various aspects of the present invention, the following examples are presented which do not limit the scope of the invention in any way.

EXAMPLES

1. Synthesis of a Dioxetaneboronic Acid.

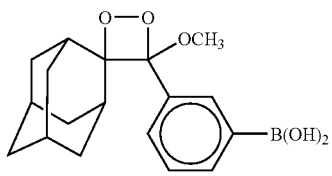

A mixture of 143.5 g of TiCl$_3$ and 17.64 g of LiAlH$_4$ was formed in 1 L of cooled anhydrous THF under Ar by slow addition of the LiAlH$_4$ to the reaction system. A black mixture resulted. Triethylamine (130 mL) was added and the mixture heated to reflux. After 1 hour at reflux a solution of 20.62 g of methyl 3-bromobenzoate and 44.02 g of adamantanone in 200 mL of anhydrous THF was added through a dropping funel over 30 min. The reaction mixture was cooled and carefully poured into a solution of 6 L of water and 300 mL of triethylamine. The mixture was extracted with 7×1 L of ethyl acetate and discarded. The ethyl acetate extracts were combined, dried over Na$_2$SO$_4$, filtered and evaporated to dryness leaving a white solid. The solid was washed several times with hexane and discarded. The hexane solutions were combined, concentrated in volume and subjected to column chromatography with 10-50% CH$_2$Cl$_2$/hexane. The alkene

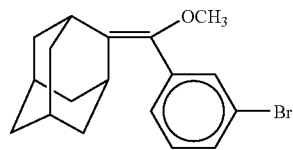

was obtained in 67% yield. $^1$H NMR (CDCl$_3$) δ 1.74-1.97 (m, 12H), 2.60 (br s, 1H), 3.24 (br s, 1H), 3.29 (s, 3H), 7.18-7.26 (m, 2H), 7.38-7.42 (m, 1H), 7.47 (s, 1H).

A solution of 2.02 g of the bromoalkene and 1.68 mL of triisopropyl borate in 10 mL of anhydrous THF and 40 mL of anhydrous toluene was formed under Ar. The solution was cooled on dry ice and treated with 2.91 mL of 2.5 M n-BuLi added over 30 min. The brown solution was stirred another hour on dry ice, warmed to room temperature and left over night. The colorless solution was quenched with 5 mL of water. The boronic acid-substituted alkene of the formula

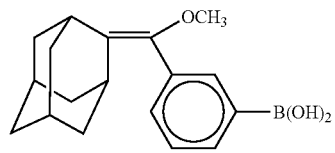

that precipitated was obtained in 98% yield. $^1$H NMR (CDCl$_3$) δ 1.78-1.97 (m, 12H), 2.67 (br s, 1H), 3.26 (br s, 1H), 3.30 (s, 3H), 7.02 (d, 1H), 7.20 (t, 1H), 7.49-7.51 (m, 2H). Reaction of a sample with 10 μL of 30% H$_2$O$_2$ resulted in its conversion to the known hydroxyalkene.

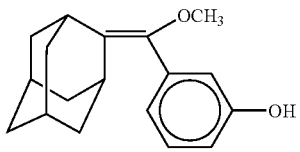

A solution of the boronic acid-substituted alkene (1.02 g) in 25 mL of methanol containing methylene blue was cooled in an ice bath. Oxygen gas was bubbled through the solution while it was irradiated with 1000 W Na lamp through a Kapton optical cutoff filter for 30 min. The solvent was evaporated and the residue purified by column chromatography with 10-30% EtOAc/hexanes followed by acetone. The boronic acid-substituted dioxetane was obtained in 68% yield. $^1$H NMR (CD$_3$OD) δ 1.01-1.06 (m, 1H), 1.22-1.29 (m, 1H), 1.51-1.92 (m, 10H), 2.15 (br s, 1H), 3.04 (br s, 1H), 3.22 (s, 3H), 7.49-8.20 (m, 4H).

2. Synthesis of Benzothiazoleboronic Acid Derivatives as Signalling Compounds for Fluorescent Detection.

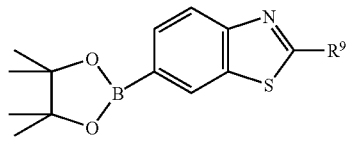

2a) R$^9$ = COOCH$_3$
2b) R$^9$ = CONH$_2$
2c) R$^9$ = CN a) Methyl 6-hydroxybenzothiazole-2-carboxylate was prepared by esterification of 6.0 g of the acid with HCl gas in 100 mL of methanol. Product (5.05 g, 79%) was isolated from the reaction by filtration, air drying and washing with CH$_2$Cl$_2$ followed by hexanes. $^1$H NMR (DMSO-d$_6$) δ 3.94 (s, 3H), 7.13 (dd, 1H), 7.50 (d, 1H), 8.01 (d, 1H).

The hydroxy group of the ester was converted to the triflate ester by reacting 5.0 g with 13.0 g of N-phenyltrifluoromethanesulfonimide in 100 mL of CHCl$_3$ and 12 mL of triethylamine at reflux for 1 h under Ar. The reaction mixture was cooled, diluted to 250 mL with CHCl$_3$ and extracted sequentially with 20% aq. citric acid, water, and satd. aq. NaHCO$_3$. The organic layer was dried and evaporated. The product triflate (6.2 g, 76%) was isolated by silica gel column chromatography with 25-100% CH$_2$Cl$_2$/hexanes. $^1$H NMR (CDCl$_3$) δ 4.12 (s, 3H), 7.51 (dd, 1H), 7.95 (d, 1H), 8.32 (d, 1H).

A reaction mixture containing 6.0 g of the triflate, 5.4 g of bis(pinacolato)diboron, 0.40 g of Pd(OAc)$_2$, 0.93 g of triphenylphosphine and 8.1 g of CsF in 80 mL of anhydrous acetonitrile was refluxed under Ar for 20 min. The mixture was cooled, diluted with acetonitrile and filtered through Celite. The filter bed was washed with CH$_2$Cl$_2$ and EtOAc. The combined filtrates were adsorbed onto dry silica and the material subjected to column chromatography with 10-30% ethyl acetate/hexanes. Product 2a was obtained (3.55 g, 60%) by evaporating pooled fractions containing the product, washing the solid with hexane and air drying. $^1$H NMR (CDCl$_3$) δ 1.38 (s, 12H), 4.09 (s, 3H), 7.98 (d, 1H), 8.22 (d, 1H), 8.47 (s, 1H).

b) Signalling compound 2a (3.05 g) was dissolved in 100 mL of methanol. Anhydrous NH$_3$ gas was bubbled through the solution causing a rise on temperature. Bubbling was continued for 10 min. The reaction flask was capped and the solution allowed to stand over night. The solvent was then evaporated to produce signalling compound 2b as a white solid 2.91 g, 100%. $^1$H NMR (CDCl$_3$) δ 1.38 (s, 12H), 5.86 (bs, 1H), 7.34 (bs, 1H), 7.9 (d, 2H), 8.08 (d, 2H), 8.47 (s, 1H).

c) Signalling compound 2b was converted to nitrile 2c with POCl$_3$. Compound 2b (0.50 g) was added to 10 mL of POCl$_3$. The mixture was stirred under a stream of Ar at 95° C. for 4 h. The mixture was cooled and evaporated to dryness. The residue was taken up in acetonitrile and poured into ice-cold saturated NaHCO$_3$ solution. A tan solid formed and was collected by filtration, washed with water and air dried. Compound 2c, 0.40 g, 85% yield. $^1$H NMR (CDCl$_3$) δ 1.38 (s, 12H), 8.04 (d, 1H), 8.21 (d, 1H), 8.46 (s, 1H).

3. Synthesis of Coumarinboronic Ester Derivatives as Signalling Compounds for Fluorescent Detection.

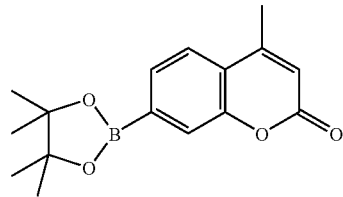

3a

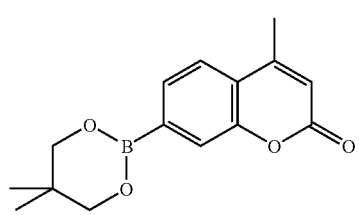

3b

7-Hydroxy-4-methylcoumarin was converted to the triflate ester by reacting 5.0 g with 15.2 g of N-phenyltrifluoromethanesulfonimide in 200 mL of CHCl$_3$ and 20 mL of triethylamine at reflux for 5 h under Ar. During the reflux period an additional 3.0 g of N-phenyltrifluoromethanesulfonimide was added. The reaction mixture was cooled over night and extracted with 2×200 mL of 10% citric acid followed by water wash. The organic layer was dried over Na$_2$SO$_4$ and evaporated. The clear colorless oil was crystallized from ether yielding the triflate ester, 8.72 g, 81%. $^1$H NMR (CDCl$_3$) δ 2.47 (s, 3H), 6.37 (s, 1H), 7.23-7.29 (m, 2H), 7.7 (d, 1H).

A reaction mixture containing 2.0 g of the triflate, 2.47 g of bis(pinacolato)diboron, 164 mg of Pd(OAc)$_2$, 372 mg of triphenylphosphine and 4.6 mL of triethylamine in 30 mL of anhydrous acetonitrile was refluxed under Ar for 4 h. The mixture was cooled and filtered through silica gel with acetonitrile. The filtrate was adsorbed onto dry silica and the material subjected to column chromatography with 0-50% ethyl acetate/hexanes. Since the product was determined to be impure it was subject to a second column using 50-100% CH$_2$Cl$_2$/hexanes. Product 3a was obtained (326 mg, 17%). $^1$H NMR (CDCl$_3$) δ 1.37 (s, 12H), 2.45 (s, 3H), 6.33 (s, 1H), 7.58 (d, 1H), 7.70 (d, 1H), 7.74 (s, 1H).

A reaction mixture containing 251 mg of the triflate, 430.6 mg of bis(neopentyl glycolato)diboron, 23 mg of Pd(Oac)$_2$, 49 mg of triphenylphosphine, 0.60 mL of triethylamine and 15 mL of anhydrous acetonitrile was refluxed under Ar for 6 h and cooled over night. The mixture was filtered through silica gel with acetonitrile. The solvent was evaporated and the residue subjected to column chromatography with 0-50% CH$_2$Cl$_2$/hexanes. Product 3b was obtained (79 mg, 36%) containing a small amount of neopentyl glycol as an impurity. $^1$H NMR (CDCl$_3$) δ 1.04 (s, 6H), 3.80 (s, 4H), 6.31 (s, 1H), 7.57 (d, 1H), 7.69 (d, 1H), 7.74 (s, 1H).

4. Synthesis of Pyreneboronic Acid Derivatives as Signalling Compounds for Fluorescent Detection.

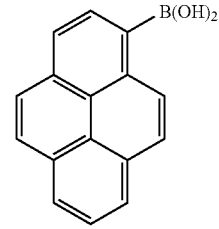

4a

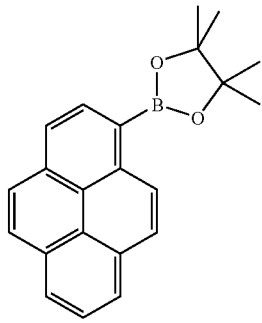

4b

A solution of 1.03 g of 2-bromopyrene in 30 mL of anh. THF was cooled to −78° C. under Ar. A solution of 1.50 mL of 2.5 M n-BuLi in hexanes was added dropwise causing a yellow precipitate to form. The reaction mixture maintained at −78° C. for another 30 min before dropwise addition of 0.42 mL of trimethylborate. After an additional 2 h at −78° C., the reaction mixture was warmed to room temperature. The reaction was quenched with 5 mL of water. Addition of $CH_2Cl_2$ caused formation of a precipitate of 381 mg of nearly pure 4a. The filtrate was evaporated and the residue chromatographed with 20-30% EtOAc/hexanes to provide an additional 76 mg of 4a. $^1$H NMR (DMSO-$d_6$) δ 7.90 (d, 1H), 8.06-8.42 (m, 7H), 9.00 (d, 1H).

A solution of 4.00 g of 2-bromopyrene, 3.97 g of bis(pinacolato)diboron, 4.19 g of KOAc, and 0.29 g of Pd(dppf)$Cl_2$, in 30 mL of anh. DMSO was put under Ar and heated at 85° C. for ca. 20 h. The mixture was cooled, poured into 200 mL of water and extracted with 3×100 mL of $CH_2Cl_2$. The combined $CH_2Cl_2$ extracts were washed with water, dried over $Na_2SO_4$ and evaporated. The residue was chromatographed on silica using 5-30% EtOAc/hexanes. Boronate ester 4b was obtained 3.61 g (78%) as a light yellow solid. $^1$H NMR (CDCl$_3$) δ 1.49 (s, 12H), 7.97-8.22 (m, 7H), 8.54 (d, 1H), 9.07 (d, 1H).

Compound 4b was converted to compound 4a by reacting 1.0 g of 4b with 1.96 g of NaIO$_4$ and 0.52 g of NH$_4$OAc in 100 mL of 50% aq. acetone with stirring for 5 days. The solution was filtered, the solids washed with 100 mL of acetone and the filtrates combined and evaporated. Compound 4a was isolated from the residue by silica gel chromatography with 30-100% EtOAc/hexanes followed by 20% MeOH/EtOAc in 86% yield.

5. Synthesis of Phenanthreneboronic Acid Derivatives as Signalling Compounds for Fluorescent Detection.

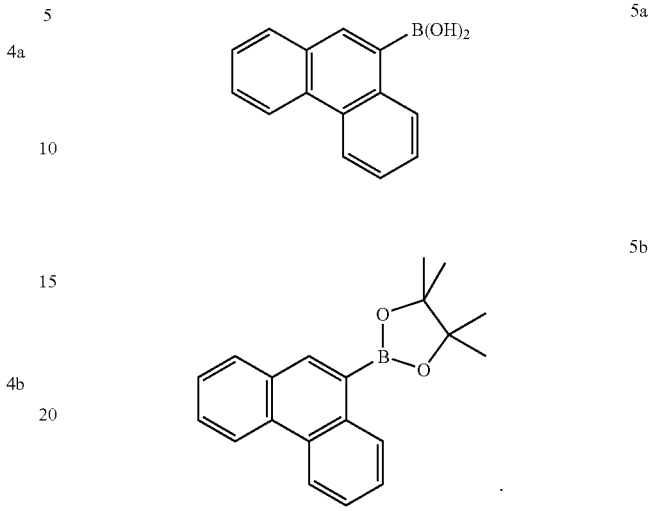

5a

5b

A solution of 2.00 g of 9-bromophenanthrene, 2.17 g of bis(pinacolato)diboron, 2.29 g of KOAc, and 0.19 g of Pd(dppf)$Cl_2$, in 10 mL of anh. DMSO was put under Ar and heated at 85° C. over night. The mixture was cooled, poured into 100 mL of water causing a white precipitate to form. The mixture was extracted with 2×100 mL of EtOAc. The combined EtOAc extracts were washed with water (emulsion!), dried over $Na_2SO_4$ and evaporated. The residue was chromatographed on silica using 10% EtOAc/hexanes. Boronate ester 5b was obtained 2.27 g (96%) as a light yellow solid. $^1$H NMR (CDCl$_3$) δ 1.46 (s, 12H), 7.55-7.70 (m, 4H), 7.94 (d, 1H), 8.39 (s, 1H), 8.66-8.73 (m, 2H), 8.81-8.85 (m, 1H).

Compound 5b was converted to compound 5a by reacting 2.07 g with 4.37 g of NaIO$_4$ and 1.15 g of NH$_4$OAc in 100 mL of 50% aq. acetone with stirring for 6 days. The solution was filtered, the solids washed with 50 mL of acetone and the filtrates combined and evaporated. Compound 5a (1.06 g, 70%) was isolated from the residue by silica gel chromatography with 30-100% EtOAc/hexanes followed by 20% MeOH/EtOAc and then washing the solid product in CHCl$_3$. $^1$H NMR (DMSO-$d_6$) δ 7.64-7.74 (m, 4H), 8.12 (d, 1H), 8.45-8.92 (m, 2H), 8.70 (s, 1H), 9.36 (d, 1H)

6. Synthesis of Anthraceneboronic Acid Derivatives as Signalling Compounds for Fluorescent Detection.

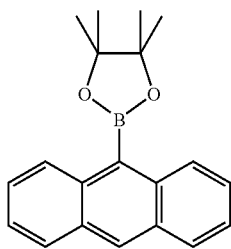

6

A solution of 2.00 g of 9-bromoanthracene, 2.17 g of bis(pinacolato)diboron, 2.29 g of KOAc, and 0.19 g of Pd(dppf)$Cl_2$, in 10 mL of anh. DMSO was put under Ar and heated at 85° C. for 24 h. The mixture was cooled, poured into 100 mL of water causing a white precipitate to form. The mixture was extracted with 3×100 mL of EtOAc. The combined ELOAc extracts were washed with water (2×100 mL), dried over $Na_2SO_4$ and evaporated. The residue was chromatographed on silica using 10-25% EtOAc/hexanes. Boronate ester 6 was obtained 1.29 g (54%) as a white solid. $^1$H NMR (CDCl$_3$) δ 1.58 (s, 12H), 7.41-7.51 (m, 4H), 7.99 (d, 2H), 8.44 (d, 2H), 8.48 (s, 1H).

7. Synthesis of Bis(benzothiazole)boronic Acid Derivatives as Signalling Compounds for Fluorescent Detection.

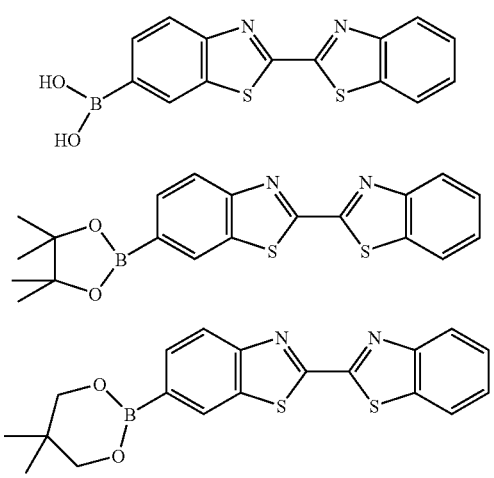

A solution of 2.0 of 6-bromo-2-cyanobenzothiazole, and 1.0 mL of 2-aminothiophenol in 100 mL of methanol was stirred under Ar for several days. The white solid was collected by filtration and washed sequentially with methanol, 2-propanol and hexane. Air drying left 2.71 g (93%) of 6-bromo-2,2'-bis(benzothiazolyl).

The bromide (0.50 g), 0.402 g of bis(pinacolato)diboron, 0.424 g of KOAc, and 35.3 mg of Pd(dppf)Cl$_2$, in 10 mL of anh. DMSO was put under Ar and heated at 85° C. over night. The mixture was cooled, poured into 200 mL of water causing a brown precipitate to form. The solid was collected by filtration and washed sequentially with water, 2-propanol and hexane. Air drying left 0.356 g (63%) of compound 7b. $^1$H NMR (CDCl$_3$) δ 1.39 (s, 12H), 7.47-7.59 (m, 2H), 7.98 (t, 2H), 8.13-8.18 (m, 2H), 8.47 (s, 1H).

The bromide (0.50 g), 0.358 g of bis(neopentylglycolato) diboron, 0.424 g of KOAc, and 35.3 mg of Pd(dppf)Cl$_2$, in 10 mL of anh. DMSO was put under Ar and heated at 85° C. over night. The mixture was cooled and filtered and the solids washed with acetone. This solid was taken up in 125 mL of CH$_2$Cl$_2$ and passed through a plug of Celite to remove residual Pd. Evaporation of solvent produced 375 mg of compound 7c (68%). $^1$H NMR (CDCl$_3$) δ 1.06 (s, 6H), 3.83 (s, 4H), 7.46-7.59 (m, 2H), 7.96-8.01 (m, 2H), 8.12-8.18 (m, 2H), 8.46 (s, 1H).

Attempted dissolution of 7c in D$_2$O for NMR analysis caused rapid hydrolysis to compound 7a. The filtrate from the initial reaction was poured into 200 mL of water causing a brown precipitate to form. The solid was collected by filtration and washed sequentially with 2-propanol and hexane to provide compound 7a. $^1$H NMR (DMSO-d$_6$) δ 7.57-7.68 (m, 2H), 8.02 (d, 1H), 8.14-8.28 (m, 3H), 8.34 (s, 1H), 8.59 (s, 1H).

8. Synthesis of Benzothiazoleboronic Acid Derivative as Signalling Compound for Luminescent Detection.

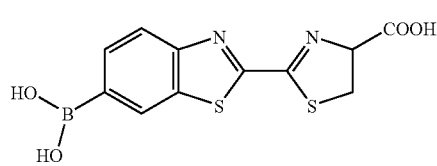

A solution of 390 mg of compound 2c in 25 mL of methanol was sparged with Ar. An Ar-sparged solution of 290 mg of D-cysteine hydrochloride in 5 mL of water adjusted to pH 8 with NaHCO$_3$ was added by pipet. An additional 5 mL of water was added to the solution. Condensation of the nitrile and cysteine was immediate so the methanol was evaporated and the remaining solution diluted to 100 mL with 20% conc. HCl. The white precipitate was collected by filtration, washed with water and air dried. Compound 8 was obtained 381 mg, 91% yield. $^1$H NMR (CDCl$_3$) δ 3.68-3.84 (sextet, 2H), 5.46 (t, 1H), 7.99 (d, 1H), 8.12 (d, 1H), 8.33 (s, 2H), 8.54 (s, 1H).

9. Synthesis of an Indoleboronic Acid Signalling Compound.

3-Bromoindole is converted to the p-toluenesulfonamide derivative by reaction with p-toluenesulfonyl chloride and triethylamine. Alternatively, indole can be protected as the SEM derivative by reaction with (Me$_3$SiOCH$_2$CH$_2$OCH$_2$Cl) SEMCl and NaH. The N-protected indole is brominated at the 3-position by reaction with pyridinium tribromide or N-bromosuccinimide. The N-protected 3-bromoindole derivative is converted to the 3-boronic acid derivative by metal-halogen exchange with t-BuLi in deoxygenated anh. THF at −78° C. followed by reaction with trimethyl or triisopropyl borate and aqueous hydrolysis. Finally the protecting group is removed. Sulfonamides are hydrolyzed by reaction with KOH in ethanol; SEM groups are removed with LiBF$_4$ in CH$_3$CN followed by aq. NaOH.

10. Chemiluminescent Detection of Hydrogen Peroxide with Boronic Acid-Substituted Dioxetane 1. The dioxetane signalling compound of Example 1 was prepared in reagent compositions containing chemiluminescence enhancers and reacted with peroxide at 37° C. The solutions contained 1 mM dioxetane and 1 mg/mL of enhancer in 0.3 M tris buffer, pH 9.35. Urea peroxide was added to achieve a final concentration of $10^{-5}$ M.

| Enhancer | t max | Imax (RLU) | Background | I/B |
|---|---|---|---|---|
| None | 5 | 10.75 | 0.282 | 38 |
| CTAB | 11.5 | 49.2 | 0.81 | 61 |
| Plus† | 25 | 1067 | 12.1 | 88 |

-continued

| Enhancer | t max | Imax (RLU) | Background | I/B |
|---|---|---|---|---|
| TB[‡] | 11.5 | 1001 | 5.9 | 170 |
| 3TB/TO[§] | 15 | >10000 | 123 | >100 |

CTAB—cetyltrimethylammonium bromide

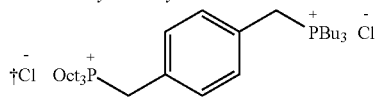

[§]poly(vinylbenzyltributylphosphonium chloride) copolymer, Compound TB in U.S. Pat. No. 5,393,469
[‡]poly(vinylbenzyltributyl(trioctyl)phosphonium chloride) copolymer, in U.S. Pat. No. 5,393,469

11. Sensitivity of Detection of Hydrogen Peroxide with a Boronic Acid-Substituted Dioxetane. A reagent composition (90 μL) containing 1 mM dioxetane signalling compound of Example 1 in 0.3 M tris buffer, pH 9.35 and 1 mg/mL of a poly(vinylbenzyltributylphosphonium chloride) copolymer, Compound TB in U.S. Pat. No. 5,393,469, was reacted with various concentrations of peroxide (10 μL) over the range 10 mM to 1 μM. Chemiluminescence intensity was measured after 4.5 min on triplicate samples. FIG. 1 shows a plot of the corrected chemiluminescence intensity as a function of the peroxide concentration in the reaction. The signal from the reaction solution with a final peroxide concentration of 1 mM was ca. 3000 times that of the blank.

15. Fluorescent Detection of Hydrogen Peroxide with 2-Naphthylboronic Acid. A solution of 1 mM 2-naphthylboronic acid was prepared in 0.2 M 221 buffer, pH 9.6. A 0.1 M stock solution of urea peroxide was prepared in deionized water. Ten-fold serial dilutions of the peroxide solution were prepared down to $1\times10^{-9}$ M. Reaction solutions containing 100 μL of 2-naphthylboronic acid solution and 100 μL of each peroxide dilution were prepared in 1 cm cuvettes. Fluorescence excitation and emission maxima for the product were 380 nm and 465 nm, respectively.

| Final [Peroxide] M | $I_{FL}$ (10 min) |
|---|---|
| $5 \times 10^{-4}$ | 103.1 |
| $5 \times 10^{-5}$ | 15.85 |
| $5 \times 10^{-6}$ | 5.76 |
| $5 \times 10^{-7}$ | 4.74 |
| Blank | 4.60 |

Figure 2:
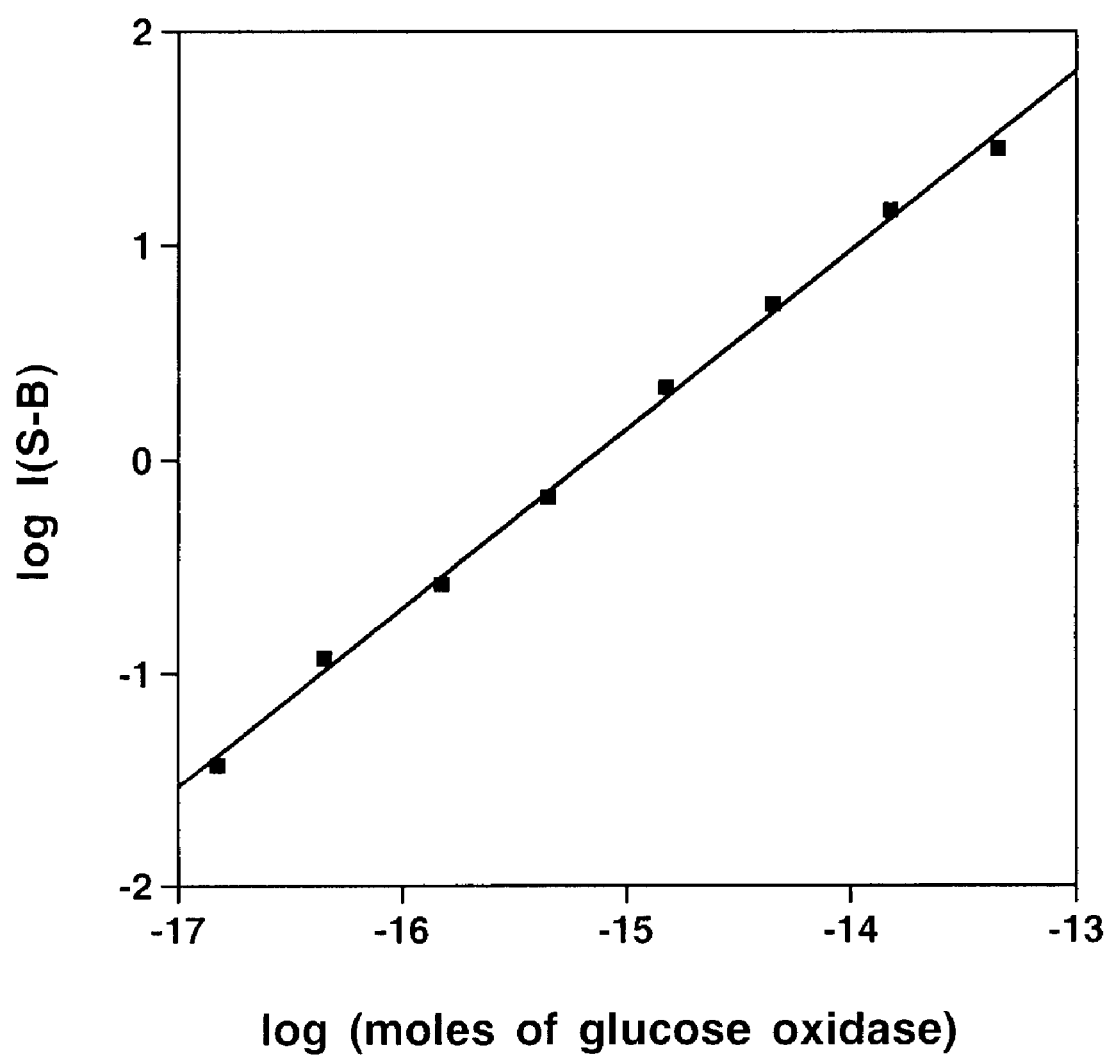
FIG. 2 is a graph relating the amount of glucose oxidase to fluorescence intensity according to Example 16. Samples containing various amounts of glucose oxidase were incubated with 0.1 M glucose for 30 min. The $H_2O_2$ produced was assayed with a reagent containing the signalling compound 2-naphthylboronic acid to produce the fluorescent compound 2-naphthol.

16. Fluorescent Detection of Glucose Oxidase with 2-Naphthylboronic Acid. Dilutions of glucose oxidase containing from $4.5\times10^{-14}$ to $1.5\times10^{-17}$ moles of enzyme in 3 μL of water were placed in triplicate white microwells. A solution of glucose (50 μL of 0.1 M) in 10 mM tris buffer, pH 7.0 was added to each well. The wells were incubated at 25° C. for 30 min. Then 50 μL portions of the reagent of Example 15 were added to each well. Fluorescence was measured after 15 min. FIG. 2 depicts the linear response of fluorescence to glucose oxidase over the range of the assay.

Figure 3:
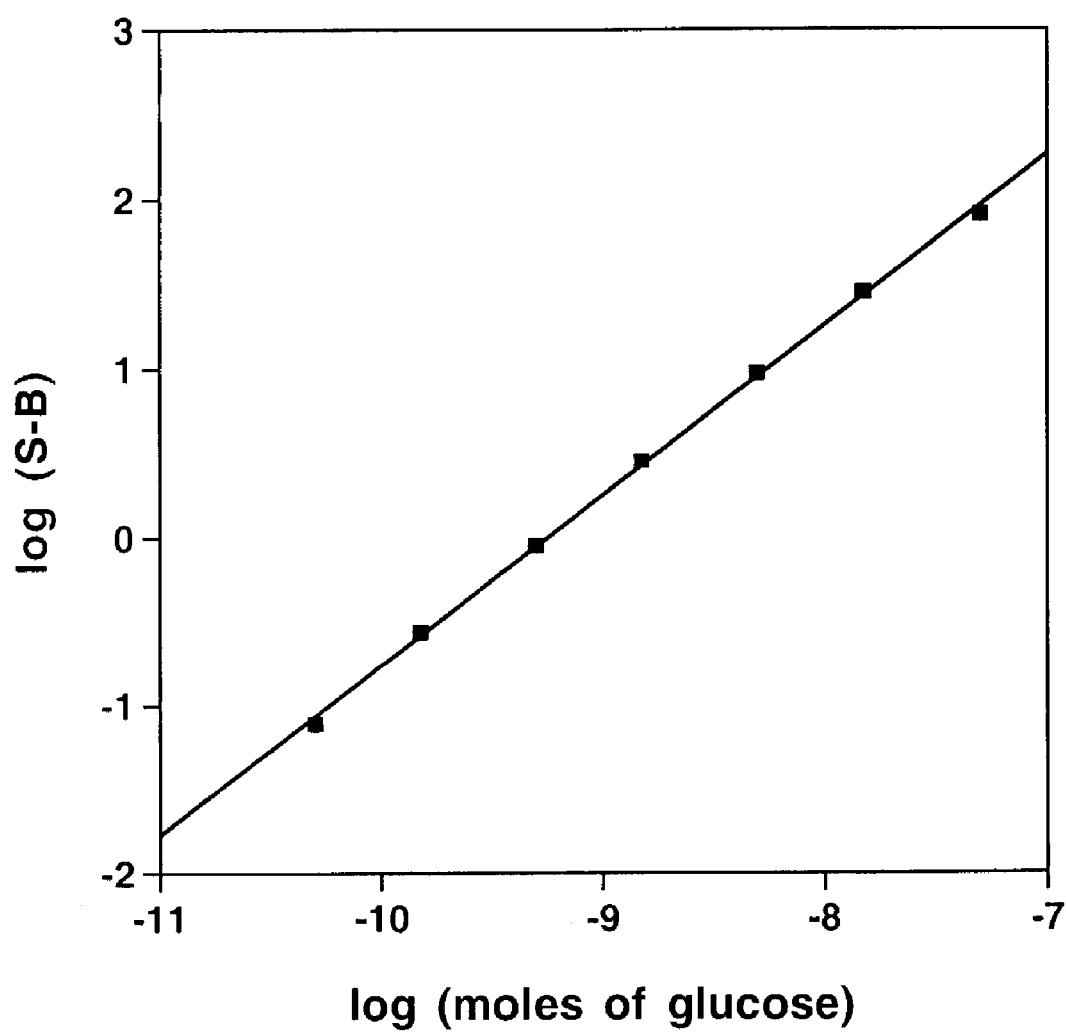
FIG. 3 is a graph relating the amount of glucose to fluorescence as described in Example 17. Samples containing various amounts of glucose were incubated at room temperature with glucose oxidase and the signalling compound 2-naphthylboronic acid. Fluorescence was measured after 30 min.

17. Fluorescent Detection of Glucose with 2-Naphthylboronic Acid. Dilutions of glucose containing between $5\times10^{-8}$ and $5\times10^{-11}$ moles of glucose in 3 μL of water were placed in triplicate white microwells. Then 100 μL portions of the reagent of Example 15 also containing $3\times10^{-7}$ M glucose oxidase were added to each well. Fluorescence was measured after 30 min. FIG. 3 depicts the linear response of fluorescence to glucose oxidase over the range of the assay.

18. Fluorescent Detection of Hydrogen Peroxide with a Bis (benzothiazolylboronate Ester. 50 μL of a 1 mM solution of the bis(benzothiazolyl)boronic acid ester 7b

Figure 4A:
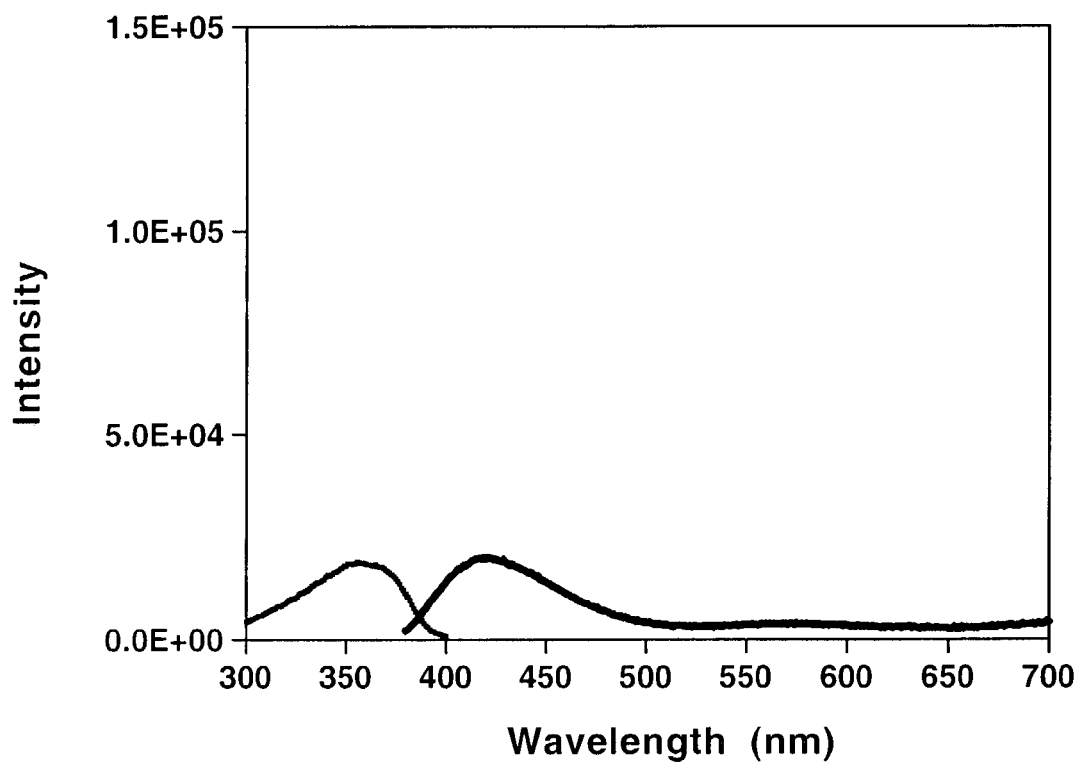
FIG. 4 is a graph depicting the fluorescence spectra of a bis(benzothiazolyl)boronate ester signalling compound before (A) and after (B) reaction with urea peroxide.
Figure 4B:
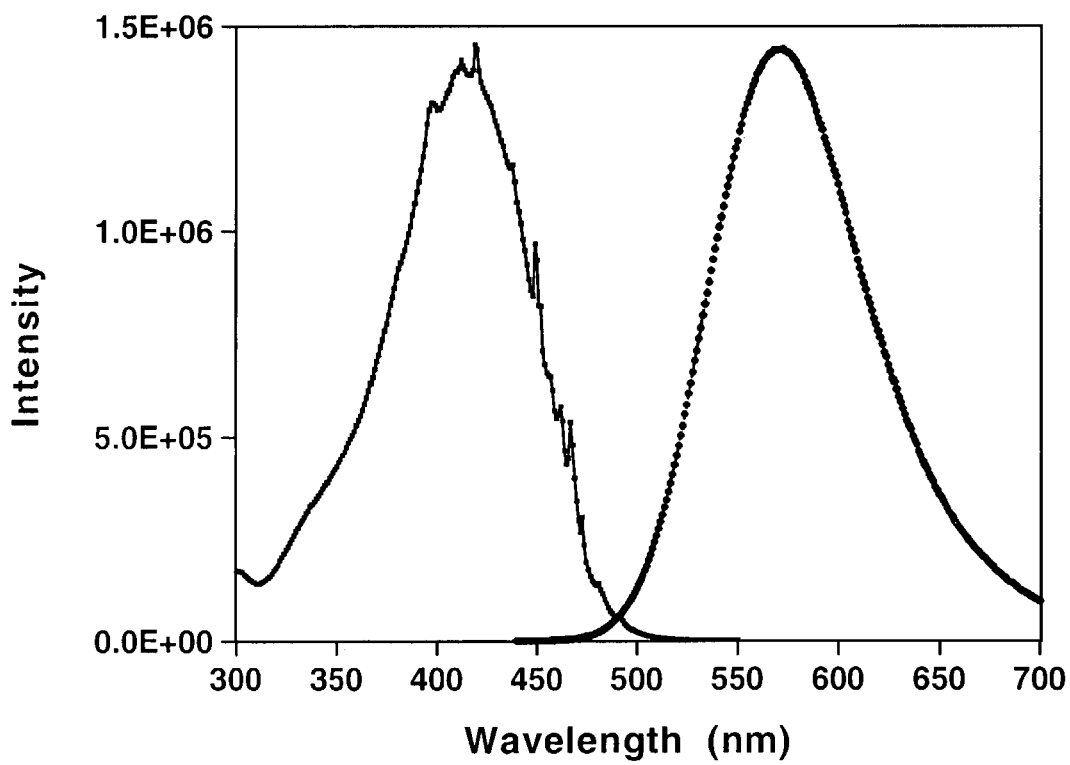

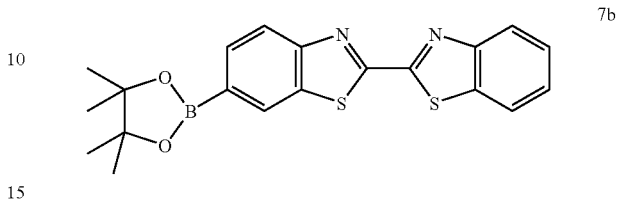

in 0.2 M 2-amino-2-methyl-1-propanol buffer, pH 9.6 was treated with aqueous solutions containing hydrogen peroxide. Fluorescence excitation and emission spectra shown in FIG. 4 were measured before and after addition of 0.1 mM urea peroxide with a Jobin Yvon/SPEX Fluoroskan spectrofluorometer. Fluorescence excitation and emission maxima for the product were 419 nm and 571 nm, respectively.

Figure 5:
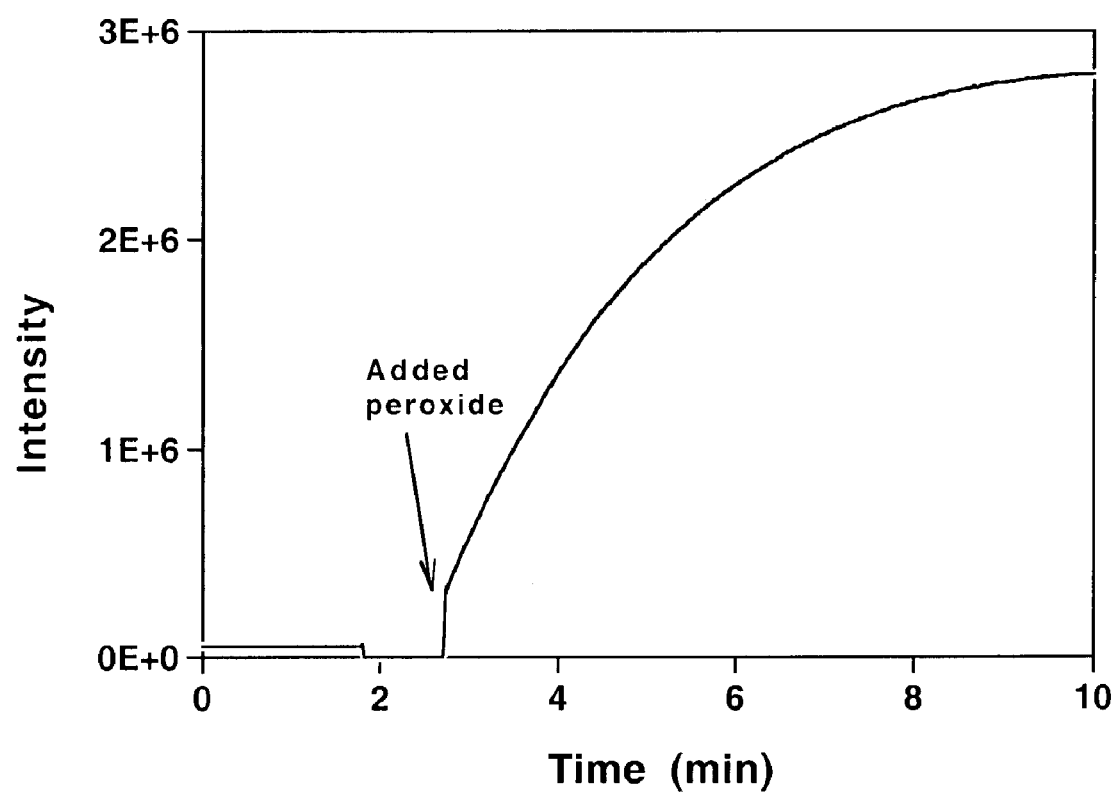
FIG. 5 is a graph depicting the grow in of fluorescence at 440 nm from the reaction of 4-methylcoumarin-7-boronic acid pinacol ester in 0.3 M tris buffer, pH 9.3 with 3 mM urea peroxide.

19. Fluorescent Detection of Hydrogen Peroxide with 4-Methylcoumarin-7-boronic Acid. A 50 μL solution of 0.5 mM 4-methylcoumarin-7-boronic acid pinacol ester in 0.3 M tris buffer, pH 9.3 was prepared. Urea peroxide was added to achieve a concentration of 3 mM. The grow-in of fluorescence at 440 nm is shown in FIG. 5.

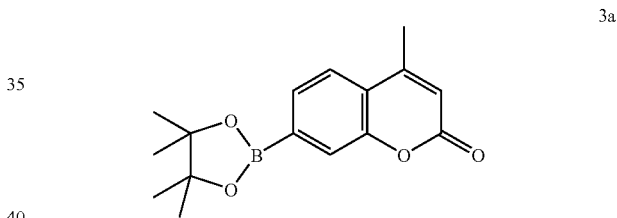

Fluorescence excitation and emission maxima for the product were 360 nm and 440 nm, respectively.

20. Fluorescent Detection of Urea Peroxide with Other Fluorescent Signalling Compounds. Procedure: A 0.1 mM solution of each of the signalling compounds listed in the table was prepared in 0.3 M tris buffer, pH 9.35. A 3 mL portion of each solution was added to a 1 cm cuvette and the emission spectrum recorded. Urea peroxide was added to each solution to achieve a concentration of 1 mM and the resulting solutions allowed to react for 15 min. The emission spectrum was recorded at this point and again after 24 hours. In each case the fluorescence of the phenolic product reached maximum intensity in 15 min and remained constant at 24 hours.

| Compound | λex (nm) | λem (nm) | Intensity (RLU) |
|---|---|---|---|
| 4a | 335 | 480 | $1 \times 10^5$ |
| 4b | 335 | 480 | $1 \times 10^5$ |
| 5a | 400 | 450 | $2 \times 10^6$ |
| 5b | 400 | 450 | $2 \times 10^6$ |

The starting boronic acid or ester signalling compounds were negligibly fluorescent under the conditions of measurement.

The maximal emission wavelengths shifted ca. 100 nm on conversion of the signalling compound to the corresponding phenolic product.

21. Colorimetric Detection of Hydrogen Peroxide with 4-Nitrophenylboronic Acid. A 20 mM stock solution of 4-nitrophenylboronic acid was prepared in ethanol and diluted 1:100 in 0.3 M tris buffer, pH 9.35 to prepare a 0.2 mM working solution A. A 1.0 M stock solution of urea peroxide was prepared in deionized water. Ten-fold serial dilutions were prepared down to $1\times10^{-9}$ M from the stock solution. Reaction solutions containing 3.0 mL of solution A and 10 μL of each peroxide dilution were prepared in 1 cm cuvettes and the absorbance at 405 nm measured in each cuvette as a function of time.

| Final [Peroxide] M | Absorbance | | | |
|---|---|---|---|---|
| | 10 min | 20 min | 60 min | 24 hours |
| $3.3 \times 10^{-3}$ | 0.183 | 0.500 | 1.393 | 3.57 |
| $3.3 \times 10^{-4}$ | 0.028 | 0.062 | 0.186 | 1.839 |
| $3.3 \times 10^{-5}$ | 0.011 | 0.013 | 0.028 | 0.249 |
| $3.3 \times 10^{-6}$ | 0.025 | 0.024 | 0.027 | 0.049 |
| $3.3 \times 10^{-7}$ | 0.013 | 0.012 | 0.013 | 0.019 |

22. Bioluminescent Detection of Hydrogen Peroxide with Boronic Acid-Substituted Compound 8. Reaction of compound 8 with hydrogen peroxide produced D-luciferin. Reaction of the generated D-luciferin with ATP, $Mg+^2$ salt and luciferase produced the characteristic greenish bioluminescence.

23. Dual Chemiluminescent/Colorimetric Detection of Hydrogen Peroxide. A solution is prepared containing the indoleboronic acid signalling compound of example 9 (0.1 mM) in 0.1 M diethanolamine buffer, pH 10. A 1.0 M stock solution of hydrogen peroxide is prepared in deionized water. Ten-fold serial dilutions are prepared down to $1\times10^{-9}$ M from the stock solution. Reaction solutions containing 2 mL of indoleboronic acid solution and 100 μL of each peroxide dilution or water for a blank were prepared in 1 cm cuvettes. A 100 μL aliquot is transferred to a luminometer tube and chemiluminescence measured after 2 min. Absorbance of the reaction solutions is measured at a suitable wavelength, e.g. 600 nm.

24. Synthesis of Additional Dioxetaneboronic Acids.

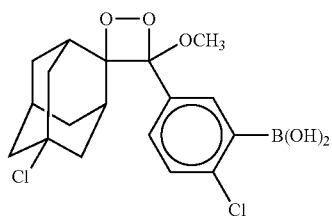

10a

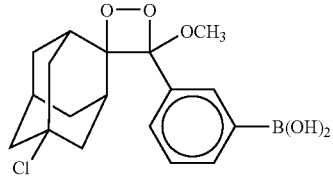

10b

Dioxetanes 10a-b are prepared by a process analogous to the one described in example 1. The known compounds 5-chloro-2-adamantanone and either methyl 4-chloro-3-bromobenzoate (for 2a) or methyl 3-bromobenzoate (for 2b) are coupled with the reagent prepared from $TiCl_3$ and $LiAlH_4$. The bromoalkene is converted to the boronic acid alkene by reaction with $B(Oi-Pr)_3$ and n-BuLi in THF followed by hydrolysis. The boronic acid alkene is photooxygenated by irradiation with a Na lamp under a stream of $O_2$ with methylene blue sensitizer to yield dioxetane 2a or 2b.

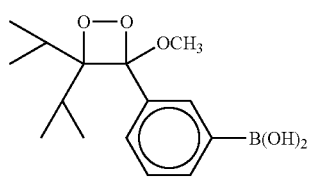

11

Dioxetane 11 is prepared by a process analogous to the one described in example 1. The known diisopropyl ketone and methyl 3-bromobenzoate are coupled with the reagent prepared from $TiCl_3$ and $LiAlH_4$. The bromoalkene is converted to the boronic acid alkene by reaction with $B(Oi-Pr)_3$ and n-BuLi in THF followed by hydrolysis. The boronic acid alkene is photooxygenated by irradiation with a Na lamp under a stream of $O_2$ with methylene blue sensitizer to yield dioxetane 11.

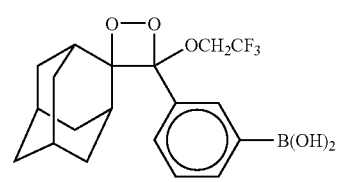

12

Dioxetane 12 is prepared by a process analogous to the one described in example 1. The known compound 3-bromo-4-chlorobenzoic acid is esterified in 2,2,2-trifluorethanol with acid catalysis to prepare the trifluoroethyl ester. Methyl 3-bromobenzoate and 2,2,2-trifluoroethyl 3-bromo-4-chlorobenzoate are coupled with the reagent prepared from $TiCl_3$ and $LiAlH_4$. The bromoalkene is converted to the boronic acid alkene by reaction with B(Oi-Pr)$_3$ and n-BuLi in THF followed by hydrolysis. The boronic acid alkene is photooxygenated by irradiation with a Na lamp under a stream of O$_2$ with methylene blue sensitizer to yield dioxetane 12.

25. Synthesis of Benzothiazoleboronic Acid Derivatives as Signalling Compounds for Luminescent Detection.

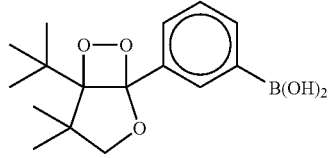

13

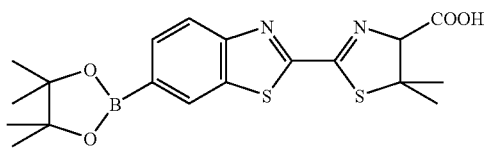

15a

Dioxetane 13 is prepared by a process analogous to that disclosed in EP 0779293A1 depicted below. Briefly, 3-bromobenzoic acid is esterified with 2,2,4,4-tetramethyl-1,3-propanediol to produce the ester (i). The alcohol function is oxidized with pyridinium chlorochromate (PCC) to form (ii). Reductive coupling of the ketone and ester groups with TiCl$_3$/LiAlH$_4$ produces the cyclic vinyl ether (iii). Conversion to the boronic acid is done with triisopropyl borate, followed by hydrolysis as described above. The double bond is photooxygenated as above to produce dioxetane 13.

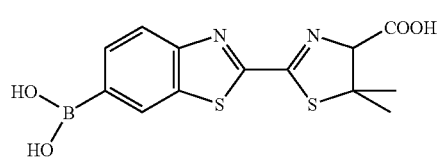

15b

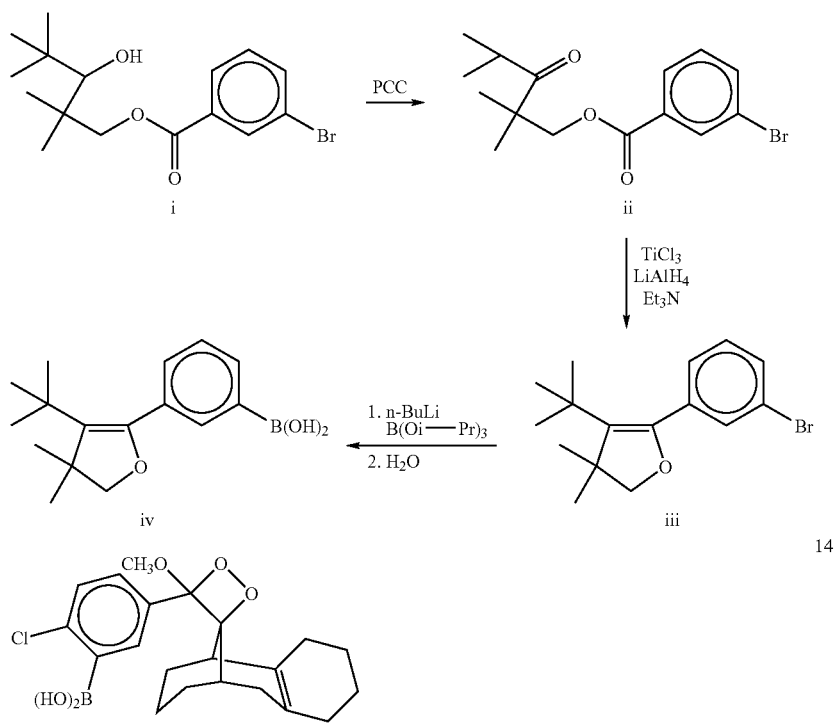

14

Dioxetane 14 is prepared by a process analogous to the one described in example 1. The known ketone tricyclo[7.3.2.0$^{2,7}$]tridec-2,7-ene-13-one (U.S. Pat. No. 6,461,876) and methyl 4-chloro-3-bromobenzoate are coupled with the reagent prepared from TiCl$_3$ and LiAlH$_4$. The bromoalkene is converted to the boronic acid alkene by reaction with B(Oi-Pr)$_3$ and n-BuLi in THF followed by hydrolysis. The boronic acid alkene is photooxygenated by irradiation with a Na lamp under a stream of O$_2$ with methylene blue sensitizer to yield dioxetane 14.

-continued

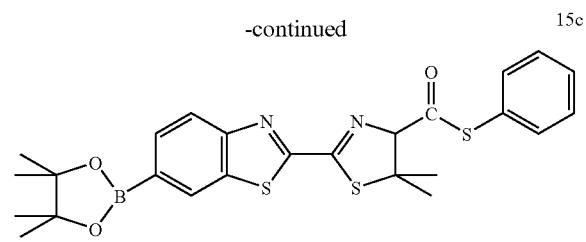

15c

A solution of 1.0 g of compound 2c and 620 mg of DL-penicillamine was prepared in 30 mL. THF. To this was added 2.0 mL of triethylamine was added followed by 3.0 mL of water. The solution was stirred for 1 h while being sparged with Ar. The solvent was evaporated, the residue taken up in $CH_2Cl_2$ and the solution dried on $MgSO_4$. Evaporation of the solvent yielded the triethylamine salt of 15a. The free acid was liberated by taking the residue up in $CH_2Cl_2$, and washing the solution with 5% aq. citric acid followed by water, drying on $MgSO_4$ and evaporation of solvent. Compound 15a was obtained 1.34 mg, 92% yield. $^1$H NMR ($CDCl_3$) δ 1.379 (s, 12H), 1.581 (s, 3H). 1.910 (s, 3H), 4.970 (s, 1H), 7.957 (d, 1H), 8.140 (d, 1H), 8.432 (s, 1H).

Treatment of the boronate ester with aq. HCl as in example 8 produces the boronic acid derivative 15b.

Compound 15a (1.0 g) and 0.44 g of carbonyl diimidazole (CDI) were added to 30 mL of anh. $CH_3CN$. The reaction was stirred under Ar for 1 h before adding 0.5 mL of thiophenol. After stirring over night the yellow precipitate was filtered, washed with $CH_3CN$ and air dried producing 0.86 g of 15c (70%). $^1$H NMR ($CDCl_3$) δ 1.383 (s, 12H), 1.577 (s, 3H). 1.845 (s, 3H), 4.939 (s, 1H), 7.451 (s, 5H), 7.962 (d, 1H), 8.152 (d, 1H), 8.440 (s, 1H).

Attempted preparation of the phenyl ester of 15a by esterification with phenol and CDI produced instead

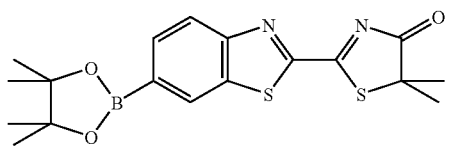

the oxidation product. This compound is useful as a fluorescent signalling compound. $^1$H NMR ($CDCl_3$) δ 1.383 (s, 12H), 2.482 (s, 3H), 2.539 (s, 3H), 7.954 (d, 1H), 8.116 (d, 1H), 8.420 (s, 1H)

The foregoing description and examples are illustrative only and not to be considered as restrictive. It is recognized that modifications of the specific compounds and methods not specifically disclosed can be made without departing from the spirit and scope of the present invention. The scope of the invention is limited only by the appended claims.

What is claimed is:

1. A method for detecting the presence or absence of hydrogen peroxide, a salt of hydrogen peroxide or a complex of hydrogen peroxide in a sample comprising:
    a) reacting the sample with a signalling compound selected from the group consisting of
    a dioxetane compound of the formula

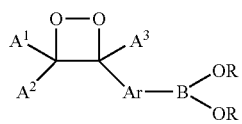

wherein $A^1$-$A^3$ represent organic groups having from 1-20 carbon atoms and Ar is an aromatic or heteroaromatic ring group, wherein $A^1$ and $A^2$ or $A^1$ and $A^3$ or $A^3$ and Ar can be combined to form a ring, a compound of the formula

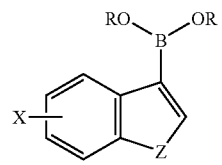

wherein Z is selected from O, S and $NR^8$, wherein $R^8$ is H or $Si(R^9)_3$, $R^9$ is $C_1$-$C_6$ alkyl or phenyl, and X represents one or two iodine, bromine or chlorine atoms, a compound of the formula

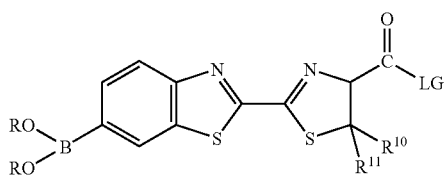

wherein LG is a leaving group and $R^{10}$ and $R^{11}$ are hydrogen, $C_1$-$C_4$ alkyl or are combined as an alkylene ring, and a compound of the formula

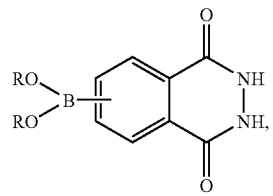

wherein B is a boron atom, and each R is independently selected from the group consisting of hydrogen, alkyl and aryl groups and can be joined together as a straight or branched alkylene chain forming a ring or as an aromatic ring;
    b) subjecting the reaction product of step (a) to conditions for a chemiluminescent reaction; and
    c) detecting chemiluminescence from the reaction of step (b), wherein the presence of chemiluminescence indicates the presence of peroxide, wherein the signalling compound itself does not undergo the chemiluminescent reaction.

2. The method of claim 1 wherein the salt of hydrogen peroxide or a complex of hydrogen peroxide is selected from the group consisting of urea peroxide, perborate salts, percarbonate salts, percarboxylic acids and percarboxylic acid salts.

3. The method of claim 2 wherein the hydrogen peroxide is produced in an enzymatic reaction.

4. The method of claim 3 wherein the enzymatic reaction is a reaction of an oxidase or dehydrogenase enzyme with a substrate for the enzyme.

5. The method of claim 4 wherein the oxidase or dehydrogenase enzyme can be present as a conjugate to a biological molecule or a member of a specific binding pair.

6. The method of claim 1 wherein the chemiluminescence signal of step (b) differs from that of the signalling compound by at least a factor of ten.

7. The method of claim 1 wherein the chemiluminescence signal of step (b) differs from that of the signalling compound by at least a factor of 100.

8. The method of claim 1 wherein the chemiluminescence signal of step (b) differs from that of the signalling compound by at least a factor of 1000.

9. The method of claim 1 further comprising, either before or concurrently with step b), reacting the detectable product with a base to initiate the production of chemiluminescence.

10. The method of claim 1 wherein the signalling compound is a dioxetane having the formula

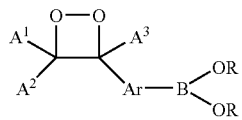

wherein $A^1$-$A^3$ represent organic groups having from 1-20 carbon atoms and Ar is an aromatic or heteroaromatic ring group and wherein $A^1$-$A^3$, Ar and R can be substituted with non-hydrogen atoms.

11. The method of claim 10 wherein $A^1$ and $A^2$ or $A^1$ and $A^3$ or $A^3$ and Ar are combined to form a ring.

12. The method of claim 10 wherein the dioxetane has the formula:

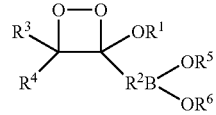

wherein $R^1$ is an organic group having from 1-20 carbon atoms which can be combined with $R^2$ or $R^3$, $R^2$ is an aromatic or heteroaromatic ring group which can include additional substituents selected from halogens, alkyl, substituted alkyl, alkoxy, substituted alkoxy, carbonyl, carboxyl, amino and alkylamino groups, $R^3$ and $R^4$ are independently selected from acyclic and cyclic organic groups containing from 3-20 carbon atoms and which can be substituted with heteroatoms, and $R^5$ and $R^6$ are independently selected from hydrogen, alkyl and aryl groups and can be joined together as a straight or branched alkylene chain forming a ring or as an aromatic ring.

13. The method of claim 11 wherein $R^3$ and $R^4$ are combined together in a cyclic or polycyclic alkyl or a cyclic or polycyclic alkenyl group which is spiro-fused to the dioxetane ring and contains 6 to 20 carbon atoms and which can include additional non-hydrogen substituents.

14. The method of claim 12 wherein $R^3$ and $R^4$ are combined together to form an adamantyl group which can be substituted with one or more substituent groups selected from halogens, alkyl, substituted alkyl, alkoxy, substituted alkoxy, carbonyl, carboxyl, phenyl, substituted phenyl, amino and alkylamino groups.

15. The method of claim 12 wherein $R^3$ and $R^4$ are each branched alkyl or cycloalkyl groups having from 3-20 carbon atoms.

16. The method of claim 12 wherein the signalling compound has the formula:

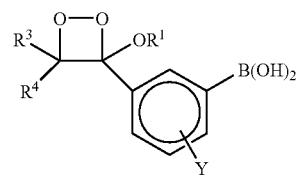

wherein Y is a substituent group selected from hydrogen, halogens, alkyl, substituted alkyl, alkoxy, substituted alkoxy, carbonyl, carboxyl, phenyl, substituted phenyl, amino and alkylamino groups.

17. The method of claim 12 wherein the dioxetane has the formula:

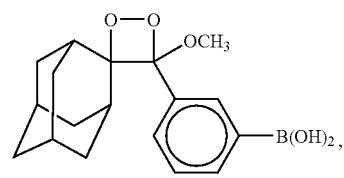

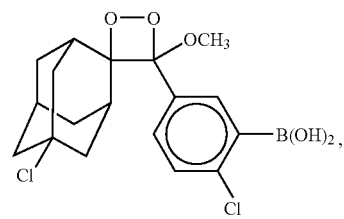

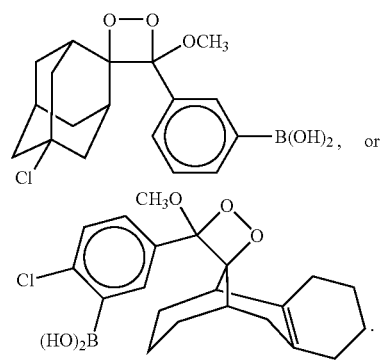

18. The method of claim 10 wherein the dioxetane has the formula:

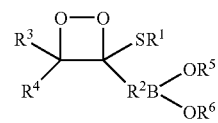

wherein $R^1$ is an organic group having from 1-20 carbon atoms which can be combined with $R^2$ or $R^3$, $R^2$ is an aromatic or heteroaromatic ring group which can include additional substituents selected from halogens, alkyl, substituted alkyl, alkoxy, substituted alkoxy, carbonyl, carboxyl, amino and alkylamino groups, and $R^3$ and $R^4$ are independently selected from acyclic and cyclic organic groups containing from 3-20 carbon atoms and which can be substituted with heteroatoms, and $R^5$ and $R^6$ are independently selected from hydrogen, alkyl and aryl groups and can be joined together as a straight or branched alkylene chain forming a ring or as an aromatic ring.

19. The method of claim 1 wherein the signalling compound has the formula:

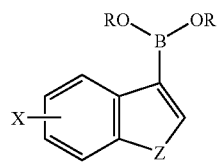

wherein Z is selected from O, S and $NR^8$, wherein $R^8$ is H or $Si(R^9)_3$, $R^9$ is $C_1$-$C_6$ alkyl or phenyl, and X represents one or two iodine, bromine or chlorine atoms and the detectable product undergoes a chemiluminescent reaction with oxygen.

20. The method of claim 1 wherein the signalling compound has the formula:

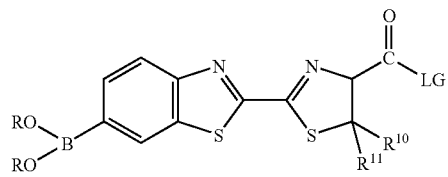

wherein LG is a leaving group and $R^{10}$ and $R^{11}$ are hydrogen, $C_1$-$C_4$ alkyl or are combined as an alkylene ring.

21. The method of claim 20 wherein the leaving group is selected from OH, $OR^{12}$, $SR^{12}$ and O-AMP groups, $R^{12}$ is a substituted of unsubstituted alkyl or aryl group, and AMP is adenosine monophosphate.

22. The method of claim 20 wherein the leaving group is selected from OH, $OR^{12}$ and $SR^{12}$, $R^{12}$ is a substituted of unsubstituted alkyl or aryl group, and wherein step (b) comprises reacting the reaction product of step (a) with a strong base and molecular oxygen to produce chemiluminescence.

23. The method of claim 20 wherein the leaving group is the O-AMP group and AMP is adenosine monophosphate and wherein step (b) comprises reacting the reaction product of step (a) with firefly luciferase enzyme and oxygen to produce chemiluminescence.

24. The method of claim 20 wherein the leaving group is the OH group and wherein step (b) comprises reacting the reaction product of step (a) with ATP, $Mg^{+2}$, firefly luciferase enzyme and oxygen to produce chemiluminescence.

25. The method of claim 1 further comprising reacting the reaction product of step (a) in the presence of at least one enhancer substance, wherein the enhancer is a quaternary onium salt alone or in combination with an anionic surfactant wherein the quaternary onium salt is selected from quaternary ammonium salts, quaternary phosphonium salts, dicationic surfactants, polymeric ammonium salts, polymeric phosphonium salts, polymeric mixed phosphonium and ammonium salts and the anionic surfactant is selected from alkyl sulfate salts and alkyl sulfonate salts.

26. A method for detecting the presence or absence of hydrogen peroxide, a salt of hydrogen peroxide or a complex of hydrogen peroxide in a sample comprising:
a) reacting the sample with a signalling compound selected from the group consisting of:

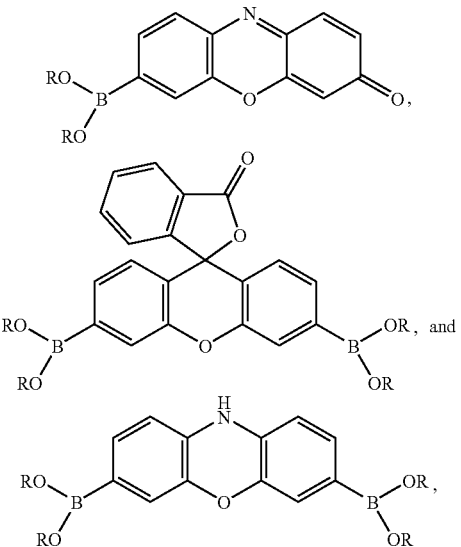

wherein B is a boron atom and wherein each R is independently selected from hydrogen, alkyl and aryl groups and can be joined together as a straight or branched alkylene chain forming a ring or as an aromatic ring;
b) irradiating the reaction product of step (a) with light of a first wavelength; and
c) detecting the presence or absence of light emitted as fluorescence at a second wavelength different from the first wavelength, wherein the presence of fluorescent signal indicates the presence of peroxide in the sample, and wherein the signalling compound itself does not emit fluorescence at the second wavelength or does so only to a very weak degree.

27. A method for detecting the presence or absence of hydrogen peroxide, a salt of hydrogen peroxide or a complex of hydrogen peroxide in a sample comprising:
a) reacting a signalling compound selected from the group consisting of:

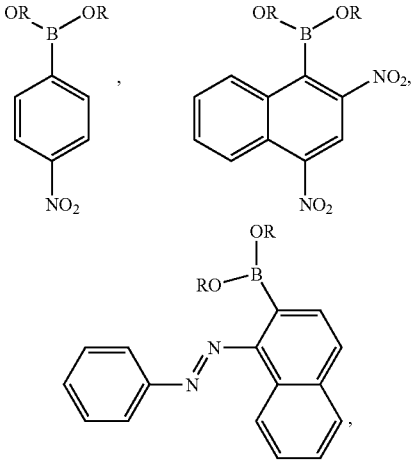

-continued

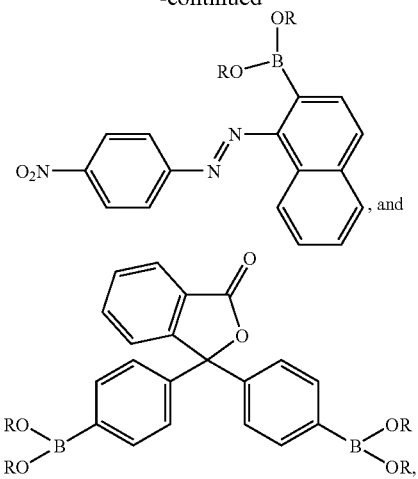

wherein B is a boron atom, and each R is independently selected from hydrogen, alkyl and aryl groups and can be joined together as a straight or branched alkylene chain forming a ring or as an aromatic ring; and b) detecting the presence or absence of the formation or change of color at a suitable chosen wavelength or range of wavelengths wherein the formation or change of color indicates the presence of peroxide, and wherein the signalling compound itself is not colored at the chosen wavelength.

28. The method of claim 1 wherein the reaction product of step (b) is detected in the presence of the starting signalling compound.

29. The method of claim 27 wherein the reaction product of step (a) is detected in the presence of the starting signalling compound.

30. The method of claim 26 wherein the reaction product of step (b) is detected in the presence of the starting signalling compound.

31. The method of claim 1 wherein the subjecting the reaction product of step (a) to conditions to cause it to undergo a chemiluminescent reaction occurs spontaneously under the conditions of the reaction.

32. The method of claim 1 wherein the subjecting the reaction product of step (a) to conditions to cause it to undergo a chemiluminescent reaction comprises adding at least one additional reagent.

33. The method of claim 32 wherein the at least one additional reagent is added after the reaction of the signaling compound with the sample.

* * * * *